United States Patent
Bennett et al.

[11] Patent Number: 5,158,078
[45] Date of Patent: Oct. 27, 1992

[54] RATE RESPONSIVE PACEMAKER AND METHODS FOR OPTIMIZING ITS OPERATION

[75] Inventors: Tommy D. Bennett, Shoreview; Lucy M. Nichols, Maple Grove, both of Minn.

[73] Assignee: Medtronic, Inc., Minneapolis, Minn.

[21] Appl. No.: 567,882

[22] Filed: Aug. 14, 1990

[51] Int. Cl.$^5$ ............................................. A61N 1/362
[52] U.S. Cl. ................................................ 128/419 PG
[58] Field of Search ................................. 128/419 PG

[56] References Cited

U.S. PATENT DOCUMENTS

| | | |
|---|---|---|
| 4,867,161 | 9/1989 | Schaldach .................. 128/419 PG |
| 4,936,304 | 6/1990 | Kresh et al. ................. 128/419 PG |
| 4,995,390 | 2/1991 | Cook et al. .................. 128/419 PG |

Primary Examiner—Kyle L. Howell
Assistant Examiner—Scott M. Getzow
Attorney, Agent, or Firm—John A. Rissman; Harold R. Patton

[57] ABSTRACT

A rate responsive cardiac pacemaker for providing an optimized pacing rate of stimulation pulses as a function of at least one selected rate control parameter. Each rate control parameter has a value which varies as a function of changes in a patient's physiologic demand an includes a sensor system for sensing the rate control parameter value and for providing a sensor output representative thereof. The cardiac pacemaker also includes control circuitry which includes a rate response defining means for deriving desired pacing rates as a function of the sensor output and an achievement monitoring means that has a predetermined achievement criterion, for monitoring the relationship between the derived pacing rates and the achievement criterion over an achievement output. An output circuitry provides optimized pacing rates as a function of the desired pacing rates; and a rate response control means adjusts the rate response defining means accordingly.

16 Claims, 16 Drawing Sheets

RATE RESPONSIVE PACEMAKER AND METHODS FOR OPTIMIZING ITS OPERATION

BACKGROUND OF THE INVENTION

1. Field of the Invention

The present invention generally relates to medical cardiac pacers, and more particularly, it pertains to a method for initializing a cardiac pacemakers of the type which responds to the patient's metabolic demand and varies the pacing rate in accordance therewith.

2. Description of the Prior Art

Early cardiac pacemakers provided a fixed-rate stimulation pulse generator that could be reset on demand by sensed atrial and/or ventricular depolarizations. Modern pacemakers include complex stimulation pulse generators, sense amplifiers and leads which can be configured or programmed to operate in single or dual chamber modes of operation, delivering pacing stimuli to the atrium and/or ventricle at fixed rates or rates that vary between an upper rate limit and a lower rate limit.

In recent years, single and dual chamber pacemakers have been developed which measure parameters which are directly or indirectly related to metabolic requirements (e.g., demand for oxygenated blood) and vary the pacing rate in response to such parameters. Such measured parameters include, for example, physical activity of the body, right ventricular blood pressure and the change of right ventricular blood pressure over time, venous blood temperature, venous blood oxygen saturation, respiration rate, minute ventilation, and various pre and post-systolic time intervals measured by impedance or pressure sensing within the right ventricle of the heart. Such sensor-driven pacemakers have been developed for the purpose of restoring rate response to exercise in patients lacking the ability to increase rate adequately by exertion.

In general, a rate responsive pacemaker includes a sensor which produces an output which varies between a maximum sensor output level and a minimum sensor output level ("Sensor Output"), and a pacing rate is provided by the pacemaker ("Pacing Rate") which typically varies as a linear or monotonic function ("f") of the sensor output between a selectable lower pacing rate ("Lower Rate") and upper pacing rate ("Upper Rate"). Function f has a selectable slope (i.e., Pacing Rate change/Sensor Output change) adjustable by means of an external programmer in conjunction with the Lower and Upper Rates. Thus, the Pacing Rate typically provided is equal to the pre-selected Lower Rate plus an increment which is a function of the measured Sensor Output, as follows:

Pacing Rate=Lower Rate+f(Sensor Output).

A human's heart rate is normally controlled by a complex set of inputs to the autonomic nervous system. No single type of sensor has been found to be entirely satisfactory for controlling rate response functions.

A significant advantage of the present invention is that each sensor's rate response will be automatically adjusted or optimized, depending upon the current gain setting's ability to achieve a pacing rate which meets the patient's ongoing metabolic needs. A further significant advantage of the present invention is that the weighting of each sensor-determined pacing rate will be automatically adjusted or optimized, depending upon the effectiveness of the sensor gain optimization, such that the pacemaker provides an optimized pacing rate to the patient. A primary benefit which flows directly from the foregoing relates to a significantly reduced need for, and frequency of, re-programming of the pacemaker. Other related benefits include: (1) better accommodation of differences, from patient to patient, in correlations between a particular sensor's output and the corresponding desired pacing rate; (2) better accommodation of differences, as to the same patient over time, in correlation between a particular sensor's output and the corresponding desired pacing rate due to physiological changes of the patient; and (3) better accommodation of differences in correlation between a particular sensor's output and the corresponding desired pacing rate due to device-related behavior, variability in components, sensor drift, etc.

Among the conventional rate responsive pacemakers, those that measure the physical activity of the patient by means of a piezoelectric transducer have become popular among the various rate responsive pacemakers. Such an activity rate responsive pacemaker is described in U.S. Pat. No. 4,485,813 issued to Anderson et al.

Some temperature sensing pacemakers have employed relatively more complex functions to take into account the initial dip in temperature due to the onset of exercise. One such pacemaker is described in U.S. Pat. No. 4,719,920 issued to Alt.

Furthermore, the decay slope of conventional pacemakers do not approximate the heart's normal behavior, in that they are programmed to follow a curve based on a single time constant. This discrepancy between the normal heart deceleration function at the end of physiologic stresses, such as physical activity, and the conventional decay function has not been totally rectified by any pacemaker presently available on the market.

Wherefore, it is desirable to have a new cardiac pacemaker and method of pacing with activity or other rate responsive dependent parameters, for responding to the patient's metabolic demand and for varying the attack and decay pacing rates in harmony with the heart's normal behavior.

At present, many physicians or clinicians set pacing parameters at the time of implant of the cardiac pacemaker, by estimating, somewhat arbitrarily, through successive trials, the approximate settings for these parameters. The numerosity of these parameters and their interactive effect on each other render the optimization process very difficult. As an abridged solution, the physicians resort to selecting extremely conservative parameter settings, even though such selections are not the optimal settings, thus causing a substantial shortening of the pacemaker life, and reducing the patient's safety.

In an effort to minimize patient problems and to prolong or extend the useful life of an implanted pacemaker, it has become common practice in recent years to provide programmable parameters in order to permit the physician to select and adjust the desired parameters to match or optimize the pacing system to the heart's physiologic requirements. The physician may adjust the output energy settings to maximize the pacemaker battery longevity while ensuring an adequate patient safety margin. Additionally, the physician may adjust the sensing threshold to ensure adequate sensing of the heart's intrinsic depolarization of cardiac tissue, while preventing oversensing of unwanted events such as myopotential interference due to upper body movements or electromagnetic interference (EMI).

Recently, rate responsive pacing systems with many programmable variables have been developed and marketed. These systems are based upon sensing a sensor derived variable that is an indicator of the patient's true metabolic and physiologic needs. Similarly, programmable parameters are required to enable to optimize this rate response function.

Wherefore, it is desirable to design a pacemaker and a method of programming the same for automatically initializing the optimal parameter settings either at the time of implant, or thereafter during subsequent followups, with minimal guess or estimation on the part of the physician the pacemaker should more accurately determine the programmable parameter values and reduce the time required to implant or conduct follow-up sessions.

One attempt at optimizing the pacing parameters is described in U.S. Pat. No. 4,867,162 issued to Schaldach. The Schaldach patent generally discloses a cardiac pacer having digital logic circuitry for choosing the characteristics of the pulses to be generated in responses to signals from several physiologic sensors detecting different exercise-related body functions.

The Schaldach pacer uses an external variable for determining the physiological exertion. This external variable is not detectable in the normal operation, but is ascertainable indirectly during the pacing operation from other physiological measured variables. Look-up tables are then used to associate the external variables to the physiological variables.

While this teaching constitutes an improvement over the conventional methods, it has not proven to be completely satisfactory in addressing and resolving the optimization problems associated with the optimization process.

The initialization process disclosed in the Schladach patent is lengthy and somewhat complicated. It generally requires high rate pacing and a substantial memory size for processing the information. Furthermore, the accuracy of the initialization might be compromised due to the extrapolation of the derived data.

Another attempt for automatically adjusting the settings is described in: "Clinical Experience with a New Activity Sensing Rate Modulated Pacemaker Using Autoprogrammability" by V. Mahaux et al., in PACE volume 12, August 1989 issue, pages 1362 through 1368. This article describes the autoprogrammability feature used in the Siemens, Elema AB's Sensolog 703 pacemaker.

The Sensolog 703 pacemaker is a single chamber activity sensing, rate modulated, multiprogrammable pulse generator whose main programmable variables include pacing mode, sensor states, minimum and maximum rates, recovery time and responsiveness. The responsiveness of the pulse generator is determined by two calibration points corresponding to two levels of exercise called "low work" (LW) and "high work" (HW). During the adjustment procedure, the physician defines the desired pacing rates for LW and HW, and asks the patient to perform the corresponding physical activites every thirty seconds. The last sensor output registered at each level of activity is compared to the desired pacing rate by an algorithm in the programmer and optimal sets of slope and threshold values are suggested. The Sensolog 703 pacemaker needs to be manually reprogrammed at various phases after implant, and various tables relating settings to corresponding slope-threshold combinations as well as tables relating rate response to sensor values are also required for programming the parameters.

It is therefore obvious that the Sensolog 703 pacemaker has not demonstrated the ease of use required for an optimal operation of the pacemaker. In fact, the physician's personal interaction is still necessitated at various phases of the automation process. Furthermore, the multi-phase automatization somewhat defeats the object behind the simplification of the operation of the pulse generator, and does not alleviate many of the problems associated with conventional programming methods.

Additionally, the proposed automization method has not attained, nor does it inspire the level of confidence expected from an automized procedure.

Similarly, other pacemakers, such as Medtronic Inc.'s Activitrax II Model 8412-14, Medtronic, Inc.'s Legend Model 8416-18, Cook Pacemaker Corporation's Sensor Model Kelvin 500, Telectronics' Meta MV Model 1202, Cordis Pacing Systems' Prism CL Model 450A, and Intermedics, Inc.'s Nova MR pacemakers have incorporated the programmability feature of various variables. However, these pacemakers generally require manual programming for entering the values of the desired parameters, in that the operating physicians estimate, through successive trials, the approximate settings for these parameters.

Medtronic Inc.'s Legend and Activitrax II are single chamber, multi-programmable, rate responsive pacemakers, whose rate responds to physical activity. These pacemakers may be programmed to the following parameters: mode, sensitivity, refractory period, pulse amplitude, pulse width, lower and upper rates and rate response gain and activity threshold.

Cook Pacemaker Corporation's Sensor Model Kelvin 500 is a unipolar, multimodal, rate responsive, processor-based pacemaker capable of monitoring the temperature of the blood in the right heart, and making the decision to increase the rate as a result of the patient's physiologic stress. This pacemaker allows for the manual programming of the following parameters: Mode, sensitivity, refractory period, pulse width, lower and upper rates, and interim rate.

Telectronics' Meta MV Model 1202 is an implantable multi-programmable bipolar cardiac pulse generator with telemetry. It can be programmed to operate in one of four pacing modes: demand inhibited (VVI or AAI); asynchronous (VOO or AOO); demand inhibited with an automatic rate response based on sensed changes in respiratory minute ventilation; or adaptive non-rate responsive mode. The following operating parameters are also programmable: Standby rate; sensitivity; pulse amplitude; pulse width; refractory period; minimum heart rate; and maximum heart rate.

Cordis Pacing System's Prism CL Model 450A is a rate responsive single-chamber, multi-programmable, implantable pulse generator with telemetry, for pacing and sensing in the ventricle. The following parameters are programmable: pacing modes (VVI, VVT, VOO); rate response (ON, OFF); electrode polarity; minimum and maximum rates; output current; pulse width; sensitivity; refractory period; and automatic calibration.

The pacer functions described in the Cordis pacemaker manual, are as follows: The target Rate Control Parameter (RCP) is the reference RCP that the pacer uses to control the pacing rate. The pacer determines what the appropriate rate should be by comparing the measured RCP to the target RCP. If the measured RCP is different from the target RCP, rate is increased or decreased until the measured RCP equals the target RCP. The target RCP is a dynamic variable which is first determined by an initialization process, which is automatically activated when rate response is programmed ON. The pacer then continuously makes automatic adjustments to the target RCP to adjust rate response.

The initial RCP is determined while the patient is at rest. During initialization, the RCP is measured for approximately 20 paced cycles to establish the target RCP. If intrinsic activity is sensed during the initialization process, initialization is temporarily suspended and the rate is increased by 2.5 ppm every cycle until pacing resumes. Once initialization is completed and the initial target RCP has been established, rate response is automatically initiated and the automatic calibration function is enabled. The pacer indicates the end of the initialization proces by issuing an ECG signature in the succeeding cycle.

The automatic calibration feature is described in the pacemaker manual as follows: When rate response is ON, the pacer continuously calibrates the target RCP while making adjustments for drifts in RCP that can occur because of lead maturation, drug therapy, and physiologic factors other than those related to emotional stress and exercise. The frequency of adjustment depends, in part, on the speed at which calibration occurs (Slow, Medium, or Fast).

Intermedics, Inc.'s Nova MR is an implantable, unipolar pulse generator designed to provide metabolic response pacing to either the atrium or ventricle. It senses variations in blood temperature and uses this information to vary the pacing rate in response to the patient's metabolic demand. The following functions are programmable to determine the pulse generator's response to variations in blood temperature: Rate response; onset detection sensitivity'; and post-exercise rate decay.

It is therefore abundantly clear that while some of these pacemakers have accomplished satisfactory results, they have not taught a method for simultaneously and automatically initializing optimal parameter settings for sensitivity threshold; pulse amplitude and width; activity threshold; and pressure (dp/dt) rate response gain, either at the time of implant, or thereafter, during subsequent follow-ups, with minimal guess or estimation on the part of the physician.

BRIEF SUMMARY OF THE INVENTION

The present invention provides a method and apparatus for controlling pacing rate in a cardiac pacemaker, which better accommodates the above-listed problems. A rate responsive cardiac pacemaker for provides an optimized pacing rate of stimulation pulses as a function of at least one selected rate control parameter. Each rate control parameter has a value which varies as a function of changes in a patient's physiologic demand an includes a sensor system for sensing the rate control parameter value and for providing a sensor output representative thereof.

The cardiac pacemaker also includes control circuitry which includes a rate response defining means for deriving desired pacing rates as a function of the sensor output and an achievement monitoring means that has a predetermined achievement criterion, for monitoring the relationship between the derived pacing rates and the achievement criterion over an achievement output.

An output circuitry provides optimized pacing rates as a function of the desired pacing rates; and a rate response control means adjusts the rate response defining means accordingly.

A significant advantage of the present invention is that each sensor's rate response will be automatically adjusted or optimized, depending upon the current gain setting's ability to achieve a pacing rate which meets the patient's ongoing metabolic needs. A further significant advantage of the present invention is that the weighting of each sensor-determined pacing rate will be automatically adjusted or optimized, depending upon the effectiveness of the sensor gain optimization, such that the pacemaker provides an optimized pacing rate to the patient. A primary benefit which flows directly from the foregoing relates to a significantly reduced need for, and frequency of, re-programming of the pacemaker. Other related benefits include: (1) better accommodation of differences, from patient to patient, in correlations between a particular sensor's output and the corresponding desired pacing rate; (2) better accommodation of differences, as to the same patient over time, in correlation between a particular sensor's output and the corresponding desired pacing rate due to physiological changes of the patient; and (3) better accommodation of differences in correlation between a particular sensor's output and the corresponding desired pacing rate due to device-related behavior, variability in components, sensor drift, etc.

The above and further objects and features of the present invention are also realized by providing a rate responsive pacemaker and a pacing method for optimizing the pacing decay curve after a period of increased activity. The pacing method includes the steps of selecting a set of predetermined achievement criteria such as an achievement rate and an achievement duration or time interval.

The achievement rate is initially selected between an upper pacing rate and a first pacing switch rate threshold. The pacing method then determines whether the achievement criterion has been met. If the achievement criterion has been met, then the decay time constant of the decay curve changes from a first value to a second value, as the pacing rate drops below the first pacing switch rate threshold.

A second pacing switch rate threshold lower than the first pacing switch rate threshold is then selected, and, if the achievement criterion has been met, then the decay time constant of the decay curve is modified from the second value to a third value, as the pacing rate drops below the second pacing switch rate threshold. The second value of the time constant for the decay curve should be longer than the first value, in order to allow a slower decay of the pacing rate. In the preferred embodiment, the third value of the time constant for the decay curve is made substantially equal to the first value. If on the other hand the achievement criteria have not been met, then the time constant of the decay curve is not modified.

The cardiac pacemaker also periodically calculates the new activity pacing rate, and then calculates the new activity target rate based upon the activity sensor output. In the preferred embodiment, the achievement rate is calculated as follows:

Achievement Rate = Lower Rate + a (Upper Rate − Lower Rate).

where "a" is a percentile value.

The first or upper pacing switch rate threshold is calculated as follows:

First Pacing Switch Rate = Lower Rate + u (Upper Rate − Lower Rate), where "u" is a percentile value.

The second or lower pacing switch rate threshold is calculated as follows:

Second Pacing Switch Rate = Lower Rate + 100% Lower Rate.

The target rate is calculated according to the following equation:

$$TR = \frac{(\text{Activity Count} + D)}{C} \cdot (32768 * 60/328).$$

In the above equations a, u, C, D, Lower Rate and Upper Rate are selectively programmable values.

By using the above inventive pacing method, the pacemaker responds to the patient's metabolic demand and varies the decay pacing rates in harmony with the heart's normal behavior, and allows for a gradual decrement in the pacing rate during the decay or deceleration period.

Additionally, the above objects and features of the present invention are realized by providing a pacemaker system and method for automatically and simultaneously optimizing and initializing a plurality of pacing parameters. The pacemaker system includes a dual sensor implantable pacemaker and an external programmer. The pacemaker includes means for automatically initializing the sensitivity threshold, pacing pulse width, pacing pulse amplitude, activity threshold, and pressure rate response gain setting.

The process of automatically initializing the sensitivity threshold includes the steps of calculating, on a periodic basis, a sense ratio factor (SRF) according to the following equation:

$$SRF = \frac{(\text{Peak Sense})}{(\text{Sense Threshold}) \times (\text{Recommended Safety Margin})}$$

where the Recommended Safety Margin is calculated as follows:

$$\text{Recommended Safety Margin} = \frac{(\% \text{ Safety Margin} + P \%)}{100}$$

and the Safety Margin is a programmable value.

The recommended sensitivity threshold is then determined according to the following equation:

Recommended Sensitivity Threshold = SRF × Programmed Threshold.

The process of automatically initializing the pacing pulse width parameter includes the steps of measuring the peak pressure values, and averaging the valid peak pressure values over a predetermined interval of time. A rheobase point is determined along a strength duration curve, and a chronaxie point is determined based on the coordinates of the rheobase.

The pulse width and amplitude parameters are then determined according to the following equations:

Recommended Pulse Width = Pulse Width of the Chronaxie.

Recommended Pulse Amplitude = $k \times$ the Pulse Amplitude of Chronaxie.

where "k" is a programmable coefficient.

The process of automatically initializing an activity threshold parameter includes the steps of setting the activity threshold to an initial value, and periodically counting the sensed activity events at rest. Thereafter, one of a plurality of higher settings for the activity threshold is automatically selected if the counter indicates a positive activity count, and one of a plurality of lower settings for said activity threshold is then automatically selected if the counter indicates a zero activity count.

The process of automatically initializing a pressure rate response gain setting position with regard to the resting dP/dt and resting rate including the steps of counting and measuring valid peak pressure values (dP/dt) and average rate. The peak pressure and rate values are averaged over a predetermined interval of time, and the resting dP/dt value is extrapolated to 70 ppm according to the following equation:

$$\text{Resting } dP/dt = \frac{[70 \text{ ppm} \times \text{Average Peak } dP/dt]}{\text{Average Resting Rate}}$$

Thereafter, the resting dP/dt value is used to set the rate response gain as follows:

$$\text{Rate Response Gain} = \frac{\text{Upper Rate} - \text{Resting Rate}}{\text{Resting } dP/dt}$$

BRIEF DESCRIPTION OF THE DRAWINGS

The above and other objects and features of the present invention and the manner of attaining them, will become apparent, and the invention itself will be best understood, by reference to the following description and the accompanying drawings, wherein:

FIG. 14A illustrates a family of ten rate response curves with different gains, for use in the automatic initialization routine of FIG. 14.

DESCRIPTION OF THE PREFERRED EMBODIMENT

Figure 1:
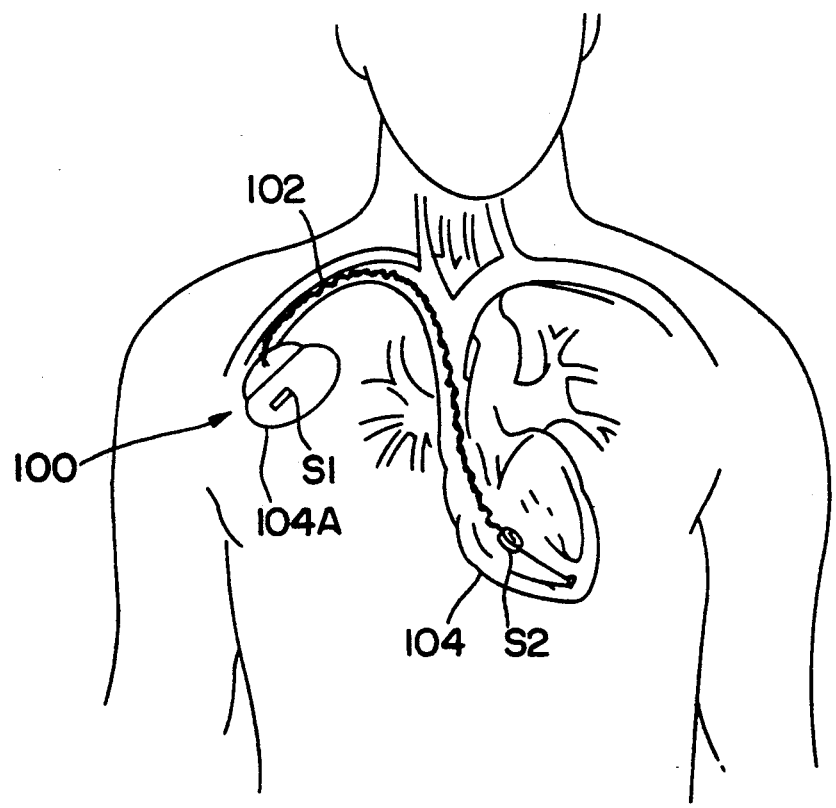
FIG. 1 graphically illustrates a multi-sensor pacemaker employing the present invention.
Figure 2:
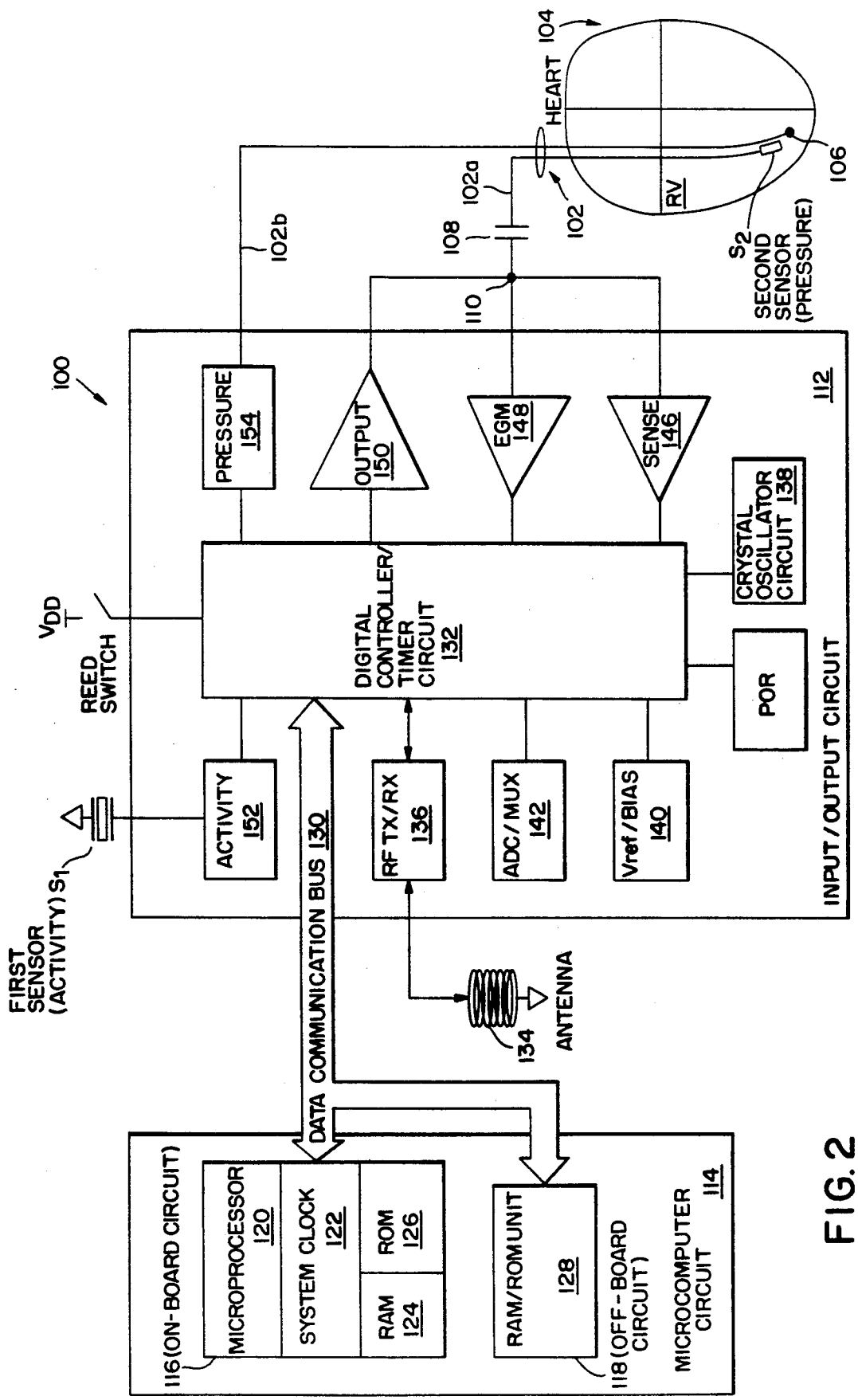
FIG. 2 is a block circuit diagram of an multi-sensor, rate-responsive, implantable, single-chamber, cardiac pacemaker having automatic rate response optimization according to the present invention.

Referring now to the drawings and more particularly to FIGS. 1 and 2 thereof, there is illustrated a multi-programmable, implantable, single-chamber, pacemaker 100 with multi-sensor rate variability and automatic rate response optimization according to the present invention. Although the present invention is described in conjunction with a microprocessor-based architecture, it will be understood that it could be implemented in digital logic-based, custom IC architecture, if desired. It will also be understood that the present invention may be implemented in dual-chamber pacemakers.

The present invention is not limited to a dual sensor pacemaker, and other sensors beside activity and pressure sensors could also be used according to the present invention. It will also be understood that while the present invention will be described in relation to the decay curve within the context of an activity-based rate responsive pacemaker, the inventive concept can be extrapolated for the attack curve, as well as for use in pressure rate responsive pacemakers.

In the preferred embodiment of FIG. 1, pacemaker 100 includes two sensors, namely, $S_1$ and $S_2$, each of which provide a sensor output which varies as a function of a measured parameter that relates to the metabolic requirements of the patient. Since each sensor output can be utilized by pacemaker 100 to control its pacing rate, each sensor output is herein referred to as a rate-control parameter (RCP). Examples of an RCP include, for example, physical activity of the body, right ventricular blood pressure and the change of right ventricular blood pressure over time, venous blood temperature, venous blood oxygen saturation, respiration rate, minute ventilation, and various pre and post-systolic time intervals measured by impedance or pressure sensing within the right ventricle of the heart.

In the preferred embodiment, first sensor $S_1$ comprises an activity sensor, such as a piezoelectric sensor of the type disclosed in U.S. Pat. No. 4,428,378 issued to Anderson et al., entitled "Rate Adaptive Pacer", which is held by the same assignee as the present invention and which is incorporated herein by reference.

First sensor $S_1$ thus measures a rate-control parameter related to physiologic forces associated with body activity ($RCP_{act}$), and provides a first sensor output (Output$_{S1}$) which is proportional to the patient's activity. Also in the preferred embodiment, second sensor $S_2$ comprises a dynamic pressure sensor, such as the type disclosed in U.S. Pat. No. 4,485,813 issued to Anderson et al., entitled "Implantable Dynamic Pressure Transducer System", which is held by the same assignee as the present invention and which is incorporated by herein by reference.

Second sensor $S_2$ thus measures a rate-control parameter related to changes in fluid pressure in the heart associated with its mechanical activity and contractility ($RCP_{press}$), and provides a second sensor output (Output$_{S2}$) which is proportional to the magnitude of the change in fluid pressure in the patient's heart. In the preferred embodiment, second sensor output$_{S2}$ is processed to derive a peak positive time derivative of the fluid pressure applied to the pressure sensor $S_2$ within the right ventricle of the patient's heart (i.e., $dP/dt_{max}$).

Pacemaker 100 is schematically shown electrically coupled via a pacing lead 102 to a patient's heart 104. Lead 102 includes an intracardiac electrode 106 and second sensor $S_2$ which are located near the distal end of lead 102 and positioned within the right ventricle (RV) of the patient's heart. Lead 102 can carry either unipolar or bipolar electrodes as is well known in the art. In the preferred embodiment, the lead 102 which couples pacemaker 100 to the ventricular endocardium can comprise a steroid-tipped, unipolar lead with an integral pressure transducer of the type described above. Electrode 106 is coupled via suitable lead conductor 102a through output capacitor 108 to node 110 and to input/output terminals of an Input/Output Circuit shown at block 112. Output from first sensor $S_1$ is coupled to Input/Output Circuit 112. Output from second sensor S₂ is also coupled to Input/Output Circuit 112 via suitable lead conductor 102b.

Input/Output Circuit 112 contains the operating input and output analog circuits for digital controlling and timing circuits necessary for the detection of electrical signals derived from the heart, such as the cardiac electrogram, output from the first sensor output $S_1$, and output from the second sensor output $S_2$, as well as for the application of stimulating pulses to the heart to control its rate as a function thereof under the control of software-implemented algorithms in a Microcomputer Circuit shown at 114.

Microcomputer Circuit 114 comprises an On-Board Circuit 116 and an Off-Board Circuit 118. On-Board Circuit 116 includes a microprocessor 120, a system clock 122, and on-board RAM 124 and ROM 126. Off-Board Circuit 118 includes an off-board RAM/ROM Unit 128. Microcomputer Circuit 114 is coupled by Data Communication Bus 130 to a Digital Controller/-Timer Circuit shown at 132. Microcomputer Circuit 114 may be fabricated of custom IC devices augmented by standard RAM/ROM components.

It will be understood that the electrical components represented in FIG. 1 are powered by an appropriate implantable-grade battery power source (not shown).

An antenna 134 is connected to Input/Output Circuit 112 for purposes of uplink/downlink telemetry through an RF Transmitter/Receiver Circuit (RF TX/RX) shown at 136. Telemetering both analog and digital data between antenna 134 and an external device, such as an external programmer, is accomplished in the preferred embodiment by means of all data first being digitally encoded and then pulse position modulated on a damped RF carrier, as substantially described in co-pending U.S. patent application Ser. No. 468,407, filed on Jan. 22, 1990, entitled "Improved Telemetry Format", which is held by the same assignee as the present invention and which is incorporated herein by reference.

A Crystal Oscillator Circuit 138, typically a 32,768 Hz crystal-controlled oscillator, provides main timing clock signals to Digital Controller/Timer Circuit 132. A Vref/Bias Circuit 140 generates a stable voltage reference and bias currents for the analog circuits of Input-/Output Circuit 112. An ADC/Multiplexor Circuit (ADC/MUX) 142 digitizes analog signals and voltages to provide telemetry and EOL function. A Power-on-Reset Circuit (POR) 144 functions as a power-on-reset system to reset function to all circuits upon detection of a low battery condition, which may occur upon initial device power-up or transiently occur in the presence of electromagnetic interference, for example.

The operating commands for controlling the timing of the pacemaker depicted in FIG. 1 are coupled by bus 128 to Digital Controller/Timer Circuit 132 wherein digital timers set the overall escape interval of the pacemaker, as well as various refractory, blanking and other timing windows for controlling the operation of the peripheral components within Circuit 132.

Digital Controller/Timer Circuit 132 is coupled to a sense amplifier (SENSE) 146 and an electrogram amplifier (EGM) 148 for receiving amplified and processed signals picked up from electrode 106 through lead conductor 102a and capacitor 108 representative of the electrical activity of the patient's heart 104. SENSE amplifier 146 produces a sense event signal for re-setting the escape interval timer within Circuit 132. The electrogram signal developed by EGM amplifier 148 is used in those occasions when the implanted device is being interrogated by the external programmer/transceiver (not shown) in order to transmit by uplink telemetry a representation of the analog electrogram of the patient's electrical heart activity as described in U.S. Pat. No. 4,556,063, issued to Thompson et al., entitled "Telemetry System for a Medical Device", which is held by the same assignee as the present invention and which is incorporated by herein by reference. An output pulse generator 150 provides the pacing stimulus to the patient's heart 104 in response to a paced trigger signal developed by Digital Controller/Timer Circuit 132 each time the escape interval times out, or an externally transmitted pacing command has been received, or in response to other stored commands as is well known in the pacing art.

Digital Controller/Timer Circuit 132 is coupled to a processing/amplifying circuit (ACTIVITY) 152 for receiving amplified and processed sensor output (Output$_{act}$) from first sensor $S_1$ and associated ACTIVITY circuitry which is representative of activity. Digital Controller/Timer Circuit 132 is coupled to a processing/amplifying circuit (PRESSURE) 154 for receiving amplified and processed sensor output (Output$_{press}$) from second sensor $S_2$ through lead conductor 102b representative of changes in fluid pressure in the patient's heart 104, for use in rate response control, and others functions as desired.

In a preferred embodiment of the present invention, pacemaker 100 is capable of operating in various non-rate-responsive modes which include VVI, VOO and VVT, as well as corresponding rate-responsive modes of VVIR, VOOR and VVTR. Further, pacemaker 100 can be programmably configured to operate such that it varies its rate only in response to one selected sensor output, or in response to both sensor outputs, if desired (i.e., utilizing either or both of Output$_{act}$ or Output$_{press}$).

DEFINITIONS

The following definition of terms used herein will assist in a better understanding of the present invention:

Achievement Count (ACH.COUNT)—A measure of the attainment of an Achievement Criterion (ACH.-CRITERION) by the Sensor Target Rate (STR) associated with each RCP-measuring sensor over a predetermined time interval which comprises the Optimization Period (OPT.PERIOD).

Achievement Criterion (ACH.CRITERION)—A value supplied by the clinician which sets an attainment threshold for each Sensor Target Rate (STR) associated with each sensor. This threshold comprises a rate component (Achievement Rate) and a time component (Achievement Duration). The Achievement Rate is a programmable percentage of the difference between the Lower Rate (LR) and the Upper Rate (UR). The Achievement Duration is a minimum time interval over which the Sensor Target Rate must exceed the Achievement Rate. With rate response, the allowed programmable values for ACH.CRITERION range from 70 ppm to 175 ppm at 1 ppm intervals, and the Achievement Duration is fixed at a four-second interval.

Activity Count (ACT.COUNT)—A measure of the output of the activity sensor (Output$_{act}$) over a predetermined interval of time. In the preferred embodiment, each event in which the amplitude of Output$_{act}$ exceeds a predetermined Activity Threshold (ACT.THRESH)

for a two-second period is counted and retained. ACT.COUNT is updated every two-second cycle, and its aggregate value comprising the count value accumulated at the end of 3 two-second cycles (i.e., after 6 seconds) is used to calculate the Sensor Target Rate for activity ($STR_{act}$).

Activity Rate Response Gain (ACT.GAIN)—A setting which corresponds to the slope of the function correlating the activity-based Sensor Target Rate ($STR_{act}$) to a value (ACT.COUNT) which corresponds to the activity sensor output ($Output_{act}$). The setting for ACT.GAIN, sometimes alternately referred to as the "activity sensor gain", corresponds to a particular rate response curve (RR). With rate response, the allowed programmable values for ACT.GAIN range from 1 to 10 at setting intervals of 1 (i.e., from RR1 to RR10).

Activity Response Time Acceleration Constant (ACT.ATTACK.TC)—A value which restricts the rate at which the activity-based Sensor Target Rate ($STR_{act}$) rate can increase, such that an activity "attack" curve provides for a more gradual and physiologically appropriate change in pacing rate. In the preferred embodiment, these time values represent the time required to reach 90% of the difference between a first steady-state activity-driven pacing period (constant activity signal input for at least a six-second interval) and a second, shorter, steady-state, activity-driven pacing period when a step increase in activity level occurs. With rate response, the allowed programmable values for ACT.ATTACK.TC are selected from those of 0.25 minutes, 0.5 minutes, or 1.2 minutes.

Activity Response Time Deceleration Constant (ACT.DECAY.TC)—A value which restricts the rate at which the activity-based Sensor Target Rate ($STR_{act}$) can decrease, such that an activity "decay" curve provides for a more gradual and physiologically appropriate change in pacing rate. In the preferred embodiment, these time values represent the time required to reach 90% of the difference between a first steady-state activity-driven pacing period (constant activity signal input for at least a six-second interval) and a second, longer, steady-state, activity-driven pacing period when a step decrease in activity level occurs. With rate response, the allowed programmable values for ACT.DECAY.TC are selected from those of 2.5 minutes, 5 minutes, or 10 minutes.

Activity Threshold (ACT.THRESH)—A minimum value which the amplitude of the activity sensor output ($Output_{act}$) must exceed to serve as input to the rate determination algorithm. The higher the threshold, the greater the amplitude necessary to become an event counted in the Activity Count (ACT.COUNT). With rate response, the allowed programmable values for ACT.THRESH range from low, medium low, medium, medium high, and high.

Lower Rate (LR)—A value supplied by the clinician which establishes a lower boundary on the pacing rate. If the sensors are disabled, or their sensor outputs are not large enough to increase rate, the lower rate is the stimulus rate. With rate response, the allowed programmable values for LR range from 40 ppm to 100 ppm at 1 ppm intervals.

Optimization Period (OPT.PERIOD)—A predetermined time interval, after which the pacemaker 100 performs its optimization of each sensor's rate response (ACT.GAIN or PRESS.GAIN) and Weighting Coefficient (COEFF), based upon the ACH.COUNT value relative to the OPT.RANGE at the expiration of each OPT.PERIOD. In the preferred embodiment, the OPT.PERIOD is established to be a twenty-four hour period.

Optimization Range (OPT.RANGE)—A range determined by the pacemaker 100 as a function of a value (Achievement Index) supplied by the clinician, which defines a minimum value (OPT.RANGE.MIN) and a maximum value (OPT.RANGE.MAX) for the Achievement Count (ACH.COUNT) during each Optimization Period (OPT.PERIOD). With rate response, the allowed programmable values for Achievement Index range from 3 to 8 at setting intervals of 1. In the preferred embodiment, pacemaker 100 determines OPT.RANGE by calculating its minimum value (OPT.RANGE.MIN) by subtracting 2 from the Achievement Index and its maximum value (OPT.RANGE.MAX) by adding 2 to the Achievement Index. Optimization for each sensor's rate response (ACT.GAIN or PRESS.GAIN) and Weighting Coefficient (COEFF) are performed by pacemaker 100 based upon the ACH.COUNT value relative to the OPT.RANGE at the expiration of each OPT.PERIOD.

Optimized Pacing Rate (OPR)—The rate at which the pacemaker 100 is to provide stimulus pulses, which is derived by pacemaker 100 based upon the Sensor Pacing Rates ($SPR_{act}$ and $SPR_{press}$) and the Weighting Coefficient (COEFF), based upon Equation 1 hereinbelow described in Part II.

Pressure (dP/dt) Average (PRESS.AVG)—Dynamic pressure sensor $S_2$ is disposed in the right ventricle (RV) of the patient's heart to sense fluid pressure therein ($RCP_{press}$), and to provide a sensor output ($Output_{press}$) related to changes in the fluid pressure associated with the heart's mechanical activity and contractility. Processing by pacemaker 100 of $Output_{press}$ yields a peak positive first time derivative thereof ($dP/dt_{max}$) which is proportional to the magnitude of such RV pressure changes. Each sensed or paced RV event will yield a peak positive $dP/dt_{max}$ signal, although a peak negative signal may be used as an alternative. In the preferred embodiment, the last 8 valid $dP/dt_{max}$ values are used to determine an average $dP/dt_{max}$ value, referred to as the "Pressure (dP/dt) Average" or "PRESS.AVG". Pacemaker 100 tests for validity of each $dP/dt_{max}$ value on a sample-by-sample basis, based upon the requirement that a sampled $dP/dt_{max}$ value must be within a predetermined range defined by a $dP/dt_{max}$ value (REST.PRESS) associated with the patient's Resting Rate (REST.RATE). In the preferred embodiment, this validity range is defined as $dP/dt_{max}$ values between 25% to 400% of REST.PRESS. Values outside this validity range are ignored. Once determined, PRESS.AVG is used to calculate the pressure-based Sensor Target Rate ($STR_{press}$) on a cycle-to-cycle basis or once upon request, according to Equation 3 hereinbelow set forth.

Pressure (dP/dt) Rate Response Gain (PRESS.GAIN)—A setting which corresponds to the slope of the function correlating the pressure-based Sensor Target Rate ($STR_{press}$) to a value (PRESS.AVG) which corresponds to the pressure sensor output ($Output_{press}$). The setting for PRESS.GAIN, sometimes alternately referred to as the "pressure sensor gain" or "dP/dt sensor gain", corresponds to a particular rate response curve (RR). With rate response, the allowed programmable (permanent) values for PRESS.GAIN range from 1 to 10 at setting intervals of 1 (i.e., from RR1 to RR10).

Pressure (dP/dt) Response Time Acceleration Constant (PRESS.ATTACK.TC)—A value which restricts the rate at which the pressure-based Sensor Target Rate (STR$_{press}$) can increase, such that a pressure "attack" curve provides for a more gradual and physiologically appropriate change in pacing rate. In the preferred embodiment, this time value represents the time required to reach 90% of the difference between a first steady-state, pressure-driven pacing period (constant dP/dt$_{max}$ signal input for at least 8 events) and a second, shorter, steady-state, pressure-driven pacing period when a step increase in dP/dt$_{max}$ level occurs. With rate response, PRESS.ATTACK.TC has a fixed value of 0.25 minutes.

Pressure (dP/dt) Response Time Deceleration Constant (PRESS.DECAY.TC)—A value which restricts the rate at which the pressure-based Sensor Target Rate (STR$_{press}$) can decrease, such that a pressure "decay" curve provides for a more gradual and physiologically appropriate change in pacing rate. In the preferred embodiment, this time value represents the time required to reach 90% of the difference between a first steady-state, pressure-driven pacing period (constant dP/dt$_{max}$ signal input for at least 8 events) and a second, longer, steady-state, pressure-driven pacing period when a step decrease in dP/dt$_{max}$ level occurs. With rate response, PRESS.DECAY.TC has a fixed value of 0.25 minutes.

Resting (dP/dt) Pressure (REST.PRESS)—The arithmetic mean of the pressure-based signal of interest (peak positive dP/dt values or dP/dt$_{max}$) measured during a predefined time interval with the patient at rest (i.e., the representative dP/dt$_{max}$ value which correlates to REST.RATE).

Resting Rate (REST.RATE)—A rate identified by the clinician during initialization for later use in the pressure-based pacing mode comprising the arithmetic mean of paced or intrinsic rates measured over a predefined time interval with the patient at rest. In the preferred embodiment, the allowed programmable values for REST.RATE range from 40 ppm to 100 ppm at 5 ppm intervals.

Safety Margin—Value supplied by the physician which specifies the ratio between the amplitude or width of a stimulus which just fails to capture and the desired amplitude or pulse width.

Sense Ratio Factor (SRF)—A ratio of a sensed signal level over the programmed threshold value.

Sensitivity—Value of the sensing amplifier threshold setting.

Sensor Pacing Rate (SPR)—The rate calculated by the pacemaker 100 in conjunction with each sensor based upon its respective Sensor Target Rate (STR) and the contribution thereto based upon its respective acceleration and deceleration function.

Sensor Target Rate (STR)—The rate calculated by the pacemaker 100 in conjunction with the activity or pressure sensors based upon programmed settings and the respective sensor output. STR does not take into account the effect which the acceleration and deceleration function produce on the Sensor Pacing Rate (SPR).

Upper Rate (UR)—A value supplied by the clinician which limits the maximum stimulation rate when the rate responsive modes for activity, pressure, or both combined, are in effect, such that the sensor-driven pacing rate generated by pacemaker 100 does not become hemodynamically excessive. With rate response, the allowed programmable values range from 100 ppm to 175 ppm at 5 ppm intervals, provided UR must also be at least 20 ppm greater than Lower Rate (LR) and Resting Rate (REST.RATE).

Weighting Coefficient (COEFF)—In a rate-response pacing mode wherein both sensors (i.e., more than one sensor) are enabled, the "Weighting Coefficient" establishes the proportion or weight of control given to each Sensor Pacing Rate (SPR) in deriving a fully-optimized rate (Optimized Pacing Rate) at which the pacemaker 100 should provide stimulus pulses (OPR). After each STR has been calculated as an intermediate rate control value from its respective Sensor Target Rate (STR), the coefficient is used in a weighting equation as a form of gain multiplier to regulate the emphasis placed on each STR in order to derive the Optimized Pacing Rate (OPR) at which the pacemaker 100 can deliver stimulus pulses. In the preferred embodiment, an OPR is calculated as follows:

$$OPR = [1 - COEFF] * SPR_{act} + (COEFF * SPR_{press}) \quad \text{(Equation 1)}$$

During initialization by the programmer, a Programmed Coefficient Value (COEFF$_{PROG}$) is also assigned by the programmer, such as a value of 0.5, to which pacemaker 100 will automatically default upon the occurrence of certain events encountered during an optimization procedure, as hereinbelow described. In the preferred embodiment, the allowed programmable values for COEFF range from 0 to 1.0 at interval settings of 0.125. During an optimization cycle at the end of the OPT.PERIOD, pacemaker 100 can automatically adjust COEFF by a step increments or decrements of 0.125, or in larger increments or decrements in a single optimization cycle under certain conditions hereinbelow described.

A brief description of measurement of the rate control parameter for activity (RCP$_{act}$) now follows. The activity sensor S$_1$ sensor employed is a piezoelectric crystal transducer of the type described in the above-mentioned '378 Anderson et al. patent, which is mounted to the interior surface of the pacemaker can as disclosed therein. Sensor S$_1$ generates a sensor output (Output$_{act}$) due to deflection of the pacemaker can as a result of compression waves within the body caused by physical movement of the body.

Processing by ACTIVITY circuit 152 is performed, such that each event in which the amplitude of Output$_{act}$ exceeds a programmed Activity Threshold (ACT.THRESH) for a predetermined time interval (i.e., a two-second cycle in the preferred embodiment) is then counted and retained in an Activity Count (ACT.COUNT) of pacemaker 100. ACT.COUNT is used to calculate the activity-based Target Rate (STR$_{act}$) on a cycle-to-cycle basis or once upon request, according to Equation 3 hereinbelow set forth in Part IV.

A brief description of measurement of the rate control parameter for pressure (RCP$_{press}$) now follows. The pressure sensor S$_2$ sensor employed is a dynamic pressure sensor of the type described in the above-mentioned '813 Anderson et al. patent. Sensor S$_2$ is disposed in the right ventricle (RV) of the patient's heart to sense fluid pressure therein (RCP$_{press}$), and to provide a sensor output (Output$_{press}$) related to changes in the fluid pressure associated with the heart's mechanical activity and contractility.

Processing by PRESSURE circuit 154 of Output$_{press}$ yields a peak positive first time derivative thereof (dP/dt$_{max}$) which is proportional to the magnitude of such RV pressure changes. Each sensed or paced RV event will yield a peak positive $dP/dt_{max}$ signal, although a peak negative signal may be used as an alternative. In the preferred embodiment, the last 8 valid $dP/dt_{max}$ values are used to determine an average $dP/dt_{max}$ value, referred to as the "Pressure (dP/dt) Average" or "PRESS.AVG".

Pacemaker 100 tests for validity of each $dP/dt_{max}$ value on a sample-by-sample basis, based upon the requirement that a sampled $dP/dt_{max}$ value must be within a predetermined range defined by a $dP/dt_{max}$ value (REST.PRESS) associated with the patient's Resting Rate (REST.RATE). In the preferred embodiment, this validity range is defined as $dP/dt_{max}$ values between 25% to 400% of REST.PRESS. Values outside this validity range are ignored. Once determined, PRESS.AVG is used to calculate the pressure-based Sensor Target Rate ($STR_{press}$) on a cycle-to-cycle basis or once upon request, according to Equation 3 hereinbelow set forth in Part IV.

It will be understood, however, that the present invention can be practiced with more than two sensors, or with sensors of a type other than the ones above described.

Figure 6A:
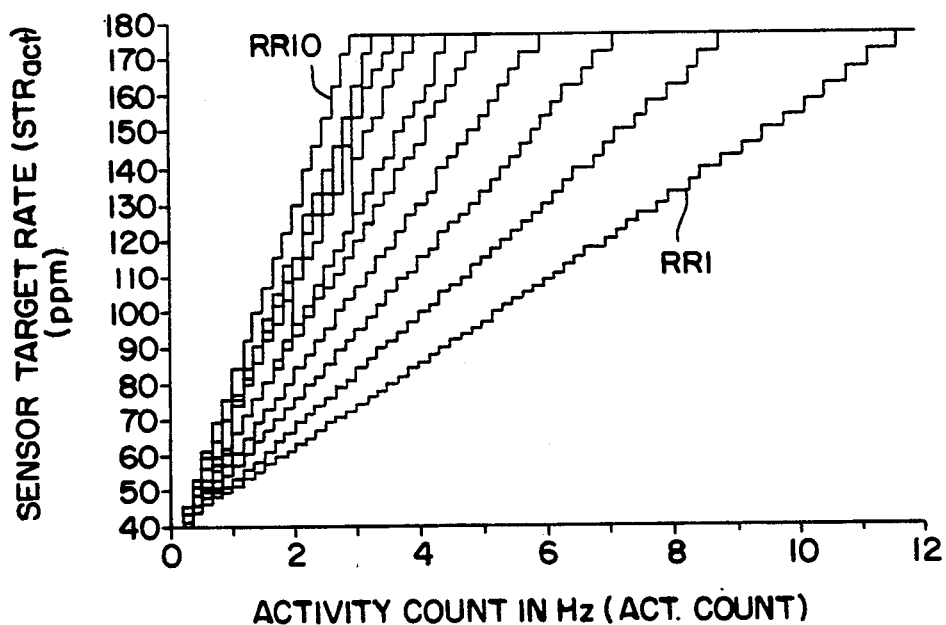
FIG. 6A is a graph illustrating multiple rate response curves correlating an output derived from a first sensor (which measures an activity-based rate control parameter) with a target pacing rate (calculated as a function of such first sensor output)
Figure 6B:
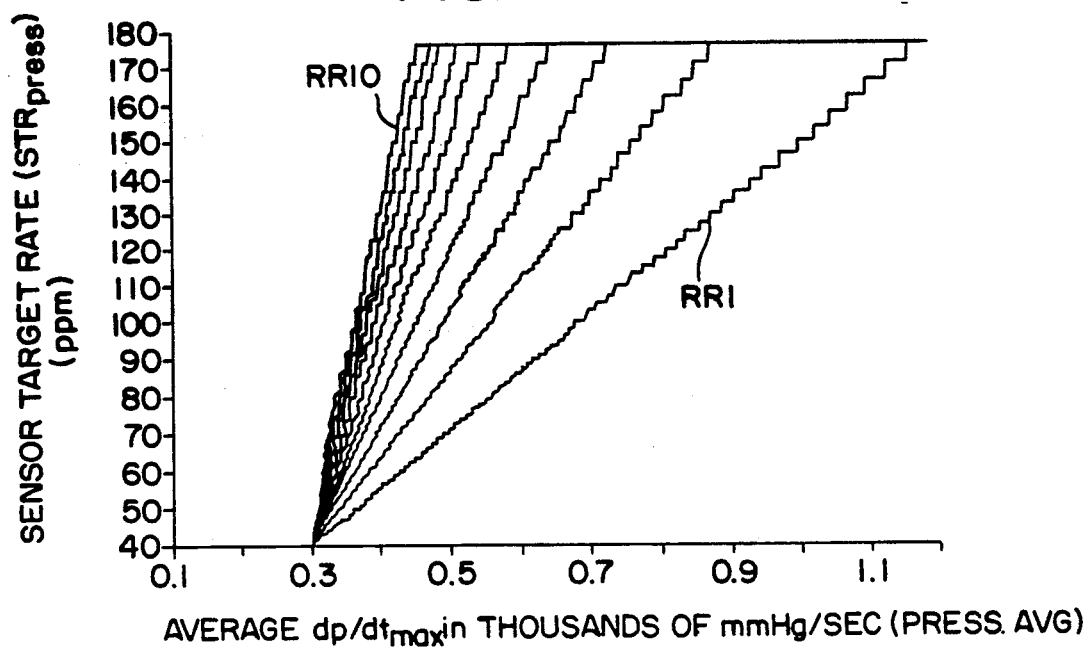
FIG. 6B is a graph illustrating multiple rate response curves correlating an output derived from a sensor (which measures a pressure-based rate control parameter) with a target pacing rate (calculated as a function of such second sensor output)

FIGS. 6A and 6B each graphically illustrate examples of a family of rate response curves for the first and second sensors $S_1$ and $S_2$, respectively. The horizontal axes of each graph correspond to sensor output values being measured. In FIG. 6A, the metric for the horizontal axis corresponds to an activity-based rate control parameter ($RCP_{act}$) and comprises the Activity Count (ACT.COUNT) as defined above, which is a function of Output$_{act}$, expressed in counts per second (Hz). In FIG. 6B, the metric for the horizontal axis corresponds to a pressure-based rate control parameter ($RCP_{press}$) and comprises the average $dP/dt_{max}$ value determined (PRESS.AVG) as defined above, which is a function of Output$_{press}$, expressed in thousands of mmHg per second. The vertical axes of each graph correspond to a Sensor Target Rate (STR), expressed in pulses per minute (ppm).

It can be seen that the Sensor Target Rate (STR) for each sensor is thus a function of the respective sensor's output, which functional correlation is defined in more detail hereinbelow. These Sensor Target Rates are utilized by pacemaker 100 in deriving the rate-responsive pacing rate for the patient's heart.

Ten rate response functions are established for each sensor, such that each function provides for excursion between selected lower and upper pacing rates within the available range of sensor outputs corresponding therewith. Multiple rate response functions are provided to afford the necessary flexibility in providing alternative rate response settings to accommodate for various factors, such as: (a) group-based correlation drift wherein differences exist among a group of patients regarding their respective correlations between the sensor output and corresponding desired pacing rate; (b) individual-based correlation drift wherein the sensor output associated with the rate control parameter being measured does not remain constant over the life of the pacemaker for an individual patient primarily due to physiological changes of the patient over time, such as due to aging; and (c) non-physiological-based correlation drift wherein the sensor output associated with the rate control parameter being measured does not remain constant over the life of the pacemaker sensor primarily due to pacemaker performance changes, such as drift in sensor output.

The various rate response functions shown in FIGS. 6A and 6B are established in conjunction with programmable parameters provided by the patient's physician using an external programmer, in a manner which is generally similar to that described in two co-pending U.S. patent applications, namely, U.S. patent application Ser. No. 455,717, filed on Dec. 22, 1989, entitled "Method and Apparatus for Implementing Activity Sensing in a Pulse Generator", and U.S. patent application Ser. No. 549,568, filed on Jul. 6, 1990, entitled "Programming Non-Volatile Memory Through Hermetic Feedthrough", which are held by the same assignee as the present invention and which are incorporated herein by reference.

The target rates for each rate control parameter are determined as follows:

(Equation 2):
$$\text{ACTIVITY SENSOR}(S_1): STR_{act} = \frac{(ACT.COUNT + D)}{C} \cdot K$$

(Equation 3):
$$\text{PRESSURE SENSOR}(S_2): STR_{press} = \frac{(PRESS.AVG + B)}{A} \cdot K$$

In the above equations, $K = (32,768 \cdot 60/328)$ and is a constant to convert clock cycle, time interval-based data to rate-based data (ppm), and A, B, C, and D constitute variables which are derived from programmed values provided by the external programmer during initialization.

Numerous programmable parameters, for example, will be established during initialization of pacemaker 100, which is described in co-pending U.S. pat. appln., filed on even date herewith, entitled "Rate Responsive Pacemaker and Method for Automatically Initializing the Same", by Bennett et al., which is held by the same assignee as the present invention and which is incorporated herein by reference. More specifically, variables A, B, C, and D are a function of the programmed Upper Rate (UR), Lower Rate (LR), and the respective rate response gain parameters (ACT.GAIN and PRESS.GAIN, for specific sensors, or RR in general), Resting Rate (REST.RATE), Resting (dP/dt) Pressure (REST.PRESS), and determine the shape desired for the various rate response curves illustrated, for example, in FIGS. 6A and 6B. Pacemaker 100 includes an arithmetic logic unit (ALU) capable of generating A, B, C and D values as a function of such programmed parameters, and for making the necessary calculations to generate the respective sensor target rates and controlling the pacemaker rate as a function thereof.

In the rate response graphs of FIGS. 6A and 6B, for example, a range of Target Rates extends between a Lower Rate (FIG. 6A) or a Resting Rate (FIG. 6B) of 40 ppm, and an Upper Rate of 175 ppm. Settings for rate response gain (ACT.GAIN and PRESS.GAIN for specific sensors, or RR in general) range from 1 to 10. It can be seen, for example, that the same magnitude of change in measured sensor output yields the greatest incremental change in target pacing rate under RR10, in contrast to the least incremental change in target pacing rate under RR1. The correlation thus defined between the sensor output and target pacing rate under these rate response curves is also often referred to as the "sensor gain function", wherein RR10 provides highest gain and RR1 provides lowest gain.

Each time the physician alters the selected values for UR. LR RR, REST.RATE and REST.PRESS via telemetry from the external programmer, these updated values are loaded into the program registers of pacemaker 100, such that new A, B, C and D values which are subsequently generated by the pacemaker 100 may be utilized by it in controlling the pacing rate as a function thereof. Regardless of which of the selected parameters has changed, the resulting function relating the Sensor Target Rate (STR) to sensor output, will take the basic form, extending from the Lower Rate (LR), or Resting Rate (REST.RATE) as appropriate, corresponding to a minimal sensor output, to the Upper Rate (UR) corresponding to an expected maximum sensor output, with a sensor output required to achieve UR decreasing as the rate response setting (RR) is increased.

The programmer should also include means for selection of acceleration and deceleration parameters which limit the rate of change in pacing rate on onset and cessation of activity, such as pacemaker 100 calculating the Sensor Pacing Rate (SPR) for each sensor as a function of its respective Sensor Target Rate (STR) and the contribution thereto based upon its respective acceleration and deceleration function. Typically, these acceleration and deceleration parameters are referred to in rate-responsive pacemakers as the attack or decay setting, respectively.

These may be expressed as the time interval required for the pacemaker to change between the current pacing interval and 90% of the desired pacing interval, assuming that the activity level corresponding to the desired pacing rate remains constant, such as provided by ACT.ATTACK.TC, ACT.DECAY.TC, PRESS.ATTACK.TC and PRESS.DECAY.TC in the preferred embodiment. A more detailed description of the use of the above-described attack/decay settings in conjunction with pacemaker 100, including a modified decay feature which provides a pacing rate which decelerates at more than one decay time constant, is described in co-pending U.S. pat. appln., filed on even date herewith, entitled "Rate Responsive Pacemaker and Pacing Method", which is held by the same assignee as the present invention and which is incorporated herein by reference.

Figure 3:
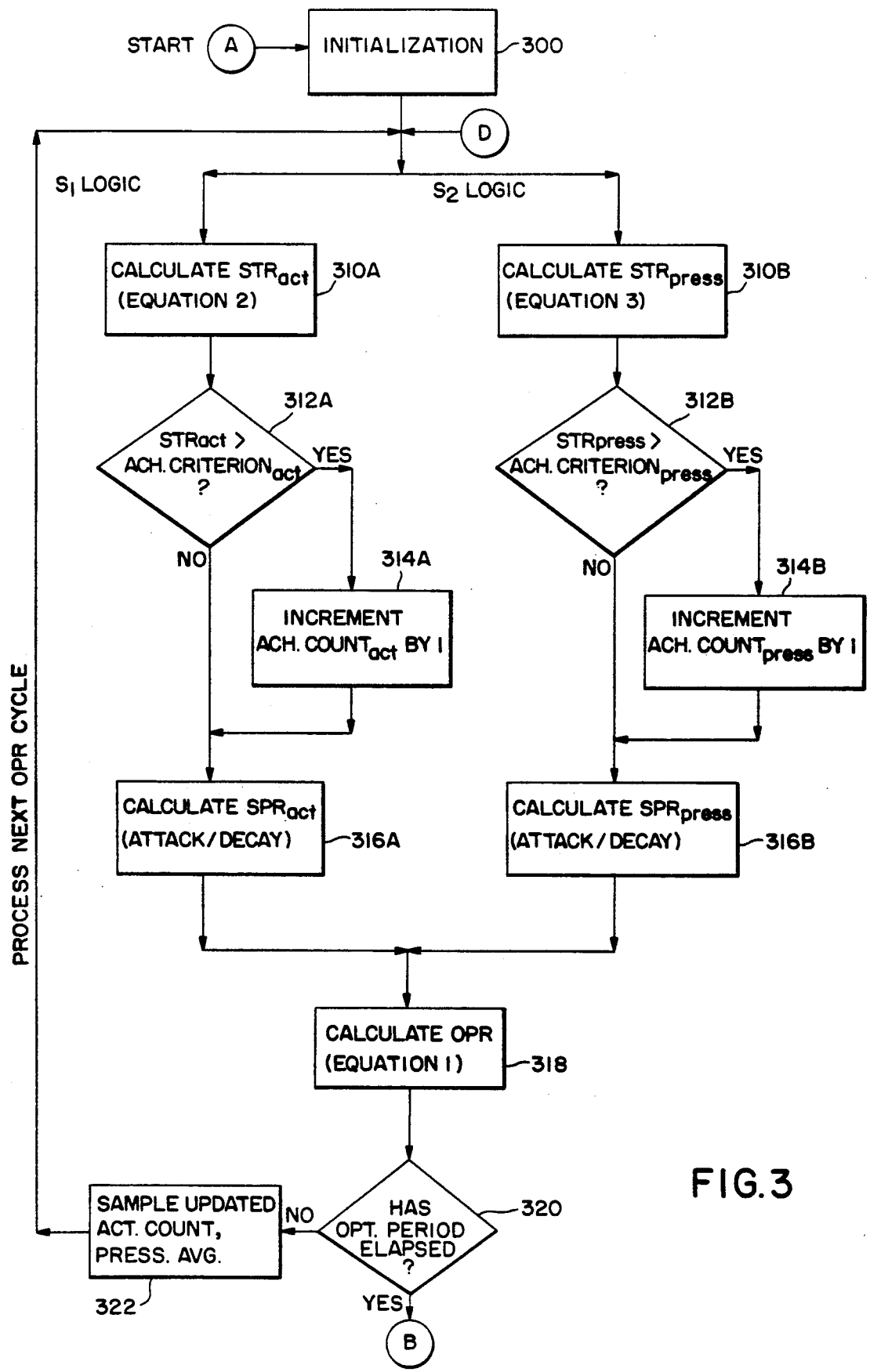
FIG. 3 is a simplified flowchart showing the basic function of software of the pacemaker of FIG. 2 for monitoring the attainment of achievement criterion for each of its sensors and for calculating an optimized pacing rate as a function thereof.

FIG. 3 is a simplified flowchart showing the basic function of software for monitoring the attainment of the Achievement Criterion by a pacemaker having at least two sensors of the type hereinabove described. It will be understood, however, that the software logic described in FIG. 3 is applicable to pacemakers having one, two or more sensors, for which an optimization of rate response as a function of an Achievement Criterion is desired.

Entering the flowchart at starting position A, block 300 corresponds to the initialization routine. At this time, the physician-selected parameters are established and programmed into storage registers in pacemaker 100 (FIG. 1) using conventional programming techniques, as hereinabove described. Various counters and flags associated with the various optimization procedures according to the present invention, which are hereinbelow described in connection with FIGS. 4 and 5, will also be initialized to the appropriate values at this time.

The remainder of FIG. 3 generally illustrates the software logic for a rate responsive pacemaker having two sensors, $S_1$ (sensing activity) and $S_2$ (sensing pressure), for purposes of monitoring the attainment of Achievement Criterion ($ACH.CRITERION_{act}$ and $ACH.CRITERION_{press}$) by each sensor's associated Sensor Target Rate ($STR_{act}$ and $STR_{press}$), throughout the duration of the Optimization Period (OPT.PERIOD). The left-hand side of FIG. 3 generally corresponds to the logic associated with $S_1$ by which its Achievement Count ($ACH.COUNT_{act}$) is incremented, and the right-side generally corresponds to the logic associated with $S_2$ by which its Achievement Count ($ACH.COUNT_{press}$) is incremented.

At blocks 310A and 310B, an STR associated with each sensor is calculated using Equations 2 and 3 hereinabove described in Part IV.

At blocks 312A and 312B, a determination is made as to whether the Achievement Criterion (ACH.CRITERION) has been met for each sensor. In particular, the STR associated with each sensor is compared with the ACH.CRITERION established for such sensor, to determine whether the STR has exceeded a threshold rate (Achievement Rate) for a predetermined time interval (Achievement Duration), and if so, the sensor's respective ACH.COUNT is incremented by 1 as shown at blocks 314A and 314B. In the preferred embodiment, since processing logistics of pacemaker 100 involve calculation of each sensor's STR in an alternating fashion, performing one STR calculation every two-second cycle, the Achievement Duration is set at 4 seconds to accommodate this operation. It will be understood, however, that these processing steps can be performed in parallel if desired, and the Achievement Duration can be shorter or longer as a function of such processing considerations.

At blocks 316A and 316B, an SPR associated with each sensor is calculated in a manner hereinabove described, based upon its most current STR and the contribution thereto required using the appropriate attack or decay function (ACT.ATTACK.TC, ACT.DECAY.TC, PRESS.ATTACK.TC and PRESS.DECAY.TC).

At block 318, assuming both sensors are enable, the Optimized Pacing Rate (OPR) which pacemaker 100 will deliver is calculated based upon the current SPR values calculated for each sensor ($SPR_{act}$ and $SPR_{press}$) and the current Weighting Coefficient (COEFF) value for the present Optimization Period, using Equation 1 hereinabove described in Part II.

At block 320, pacemaker 100 determines whether the predetermined time interval associated with the Optimization Period (OPT.PERIOD) has elapsed. If not, pacemaker resumes processing additional cycles, in the manner described above. Once OPT.PERIOD has elapsed, pacemaker logic associated with optimization is initiated by exiting this flowchart at exit position B to commence optimization logic shown in FIGS. 4 and 5. In the preferred embodiment, OPT.PERIOD is selected at twenty-four hours, using crystal oscillator 138 which provides a real-time clock function.

It will be understood that OPT.PERIOD can be set to be shorter or longer time intervals, if desired. A setting at 24 hours, however, is believed to provide a time interval which is an appropriate length to permit sufficient rate-response related data to be gathered between optimization procedures, while optimizing at a frequency which accommodates most patient's needs, including chronobiologic behaviors such as circadian rhythm. OPT.PERIOD can alternatively be set, for example, to multiples of twenty-four periods for accommodation of variations in patients' behavior, such as infradian rhythms or other factors.

Figure 4:
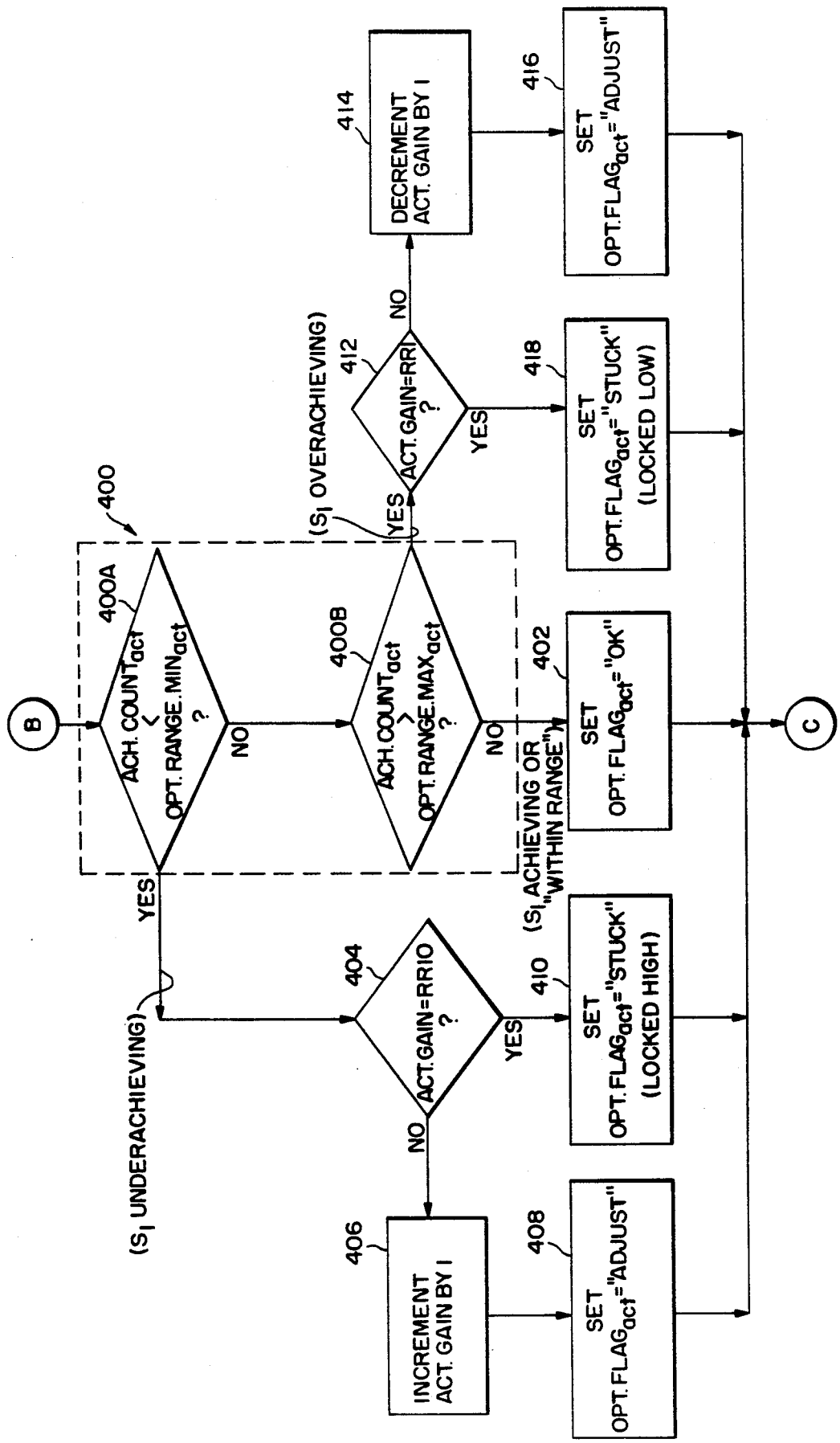
FIG. 4 is a simplified flowchart showing the basic function of software of the pacemaker of FIG. 2 for varying a sensor's rate response or gain as a function of its achievement criterion, such that the sensor's gain is automatically adjusted for purposes of deriving an optimized pacing rate.
Figure 5:
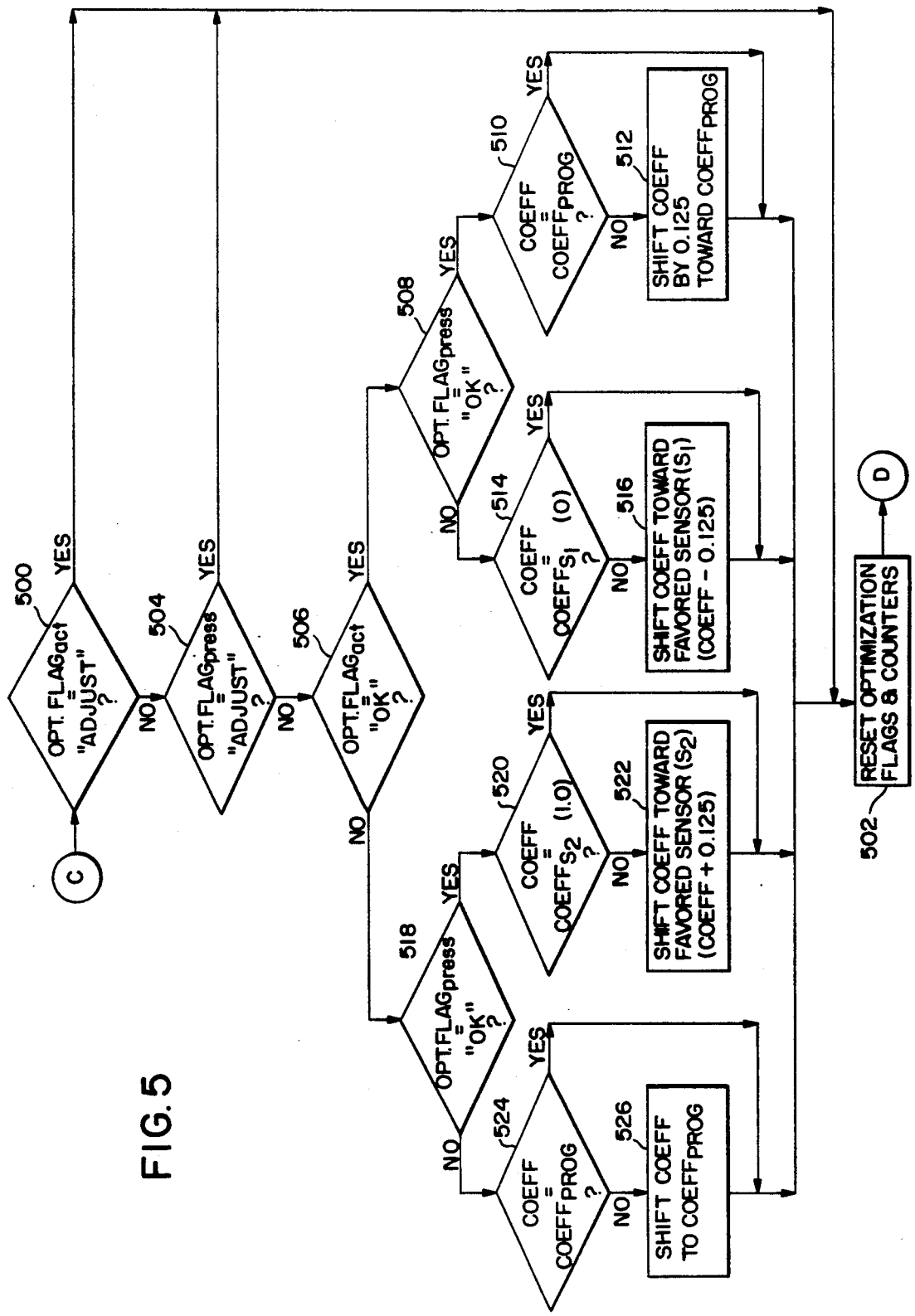
FIG. 5 is a simplified flowchart showing the basic function of software of the pacemaker of FIG. 2 for varying a sensor weighing coefficient as a function of each of the sensor's achievement criterion and sensor gain adjustment, such that the weighing given to each sensor's output and target pacing rate are automatically adjusted for purposes of deriving an optimized pacing rate.

FIGS. 4 and 5 are simplified flowcharts showing the basic function of software for performing optimization accoording to the present invention, for purposes of optimizing the rate of stimulus pulses (Optimized Pacing Rate or "OPR") being provided by pacemaker 100.

FIG. 4 relates to a sensor gain optimization procedure, useful in the context of a single or a multiple sensor-driven rate-responsive pacemaker, wherein a sensor's rate response or gain is varied as a function of its Achievement Criterion.

FIG. 5 relates to a sensor weighting optimization procedure, useful in the context of a multiple sensor-driven, rate-responsive pacemaker, wherein a sensor weighting coefficient (Weighting Coefficient or "COEFF") is varied as function of the rate response or gain adjustments which were made (i.e., varied from RR1 to RR10), if possible, for each sensor during the sensor gain optimization procedure. Thus, the Weighting Coefficient (COEFF) is varied as a function of the Achievement Criterion for each of the sensors, such that the proportion or weight of control given to each sensor's output is regulated appropriately for purposes of deriving an Optimized Pacing Rate for the patient.

The overall control logic of optimization according to the present invention, described in the simplified context of a two-sensor application, can be summarized as follows:

A. General Rules for Optimization (1) The Optimization Range (OPT.RANGE) for each sensor is defined by a minimum value (OPT.RANGE.MIN) and a maximum value (OPT.RANGE.MAX). At the end of each Optimization Period (OPT.PERIOD), during each optimization cycle, the Achievement Count (ACH.COUNT) for each sensor is compared to its respective OPT.RANGE. Based upon such comparison, a sensor gain optimization (adjusting each sensor's rate response or gain (ACT.GAIN or PRESS.GAIN)) and/or a sensor weighting optimization (adjusting a Weighting Coefficient (COEFF)) are performed, if appropriate, by pacemaker 100 at the end of each OPT.PERIOD.

(2) A sensor gain is characterized as "underachieving" if its ACH.COUNT is less than the OPT.RANGE.MIN.

(3) A sensor gain is characterized as "overachieving" if its ACH.COUNT is greater than the OPT.RANGE.MAX.

(4) A sensor gain is characterized as "within range" or "achieving its criteria" if its ACH.COUNT is greater than or equal to its OPT.RANGE.MIN and less than or equal to its OPT.RANGE.MAX.

(5) A sensor gain is characterized as at "minimum gain" if it is set at its lowest available rate response setting (shown, for example, as RR1 in FIGS. 6A and 6B).

(6) A sensor gain is characterized as at "maximum gain" if it is set at its highest available rate response setting (shown, for example, as RR10 in FIGS. 6A and 2B).

(7) A sensor gain is characterized as "locked low" or "stuck" if, during the current optimization cycle, it is desired to decrease the sensor gain but it is already set at its lowest available rate response setting (e.g., RR1) due to an adjustment from a previous optimization cycle.

(8) A sensor gain is characterized as "locked high" or "stuck" if, during the current optimization cycle, it is desired to increase the sensor gain but it is already set at its highest available rate response setting (e.g., RR10) due to an adjustment from a previous optimization cycle.

(9) Adjustments to sensor gain (RR) are made in step increments or decrements of one setting at a time per optimization cycle (e.g., from RR3 to RR4).

(10) Adjustments to Weighting Coefficient (COEFF) are generally made in single step increments or decrements of 0.125 per optimization cycle based upon certain conditions encountered as specified below for the sensor weighting optimization procedure. A Programmed Coefficient Value ($COEFF_{PROG}$) is programmed during initialization with a desired value which will be used as an initial COEFF value for the first optimization procedure. Under certain conditions encountered during sensor weighting optimization as specified hereinbelow, the COEFF will be shifted during an optimization cycle from its current value toward the $COEFF_{PROG}$ in single step increments (or decrements), or in a multi-step increment (or decrement).

(11) In the preferred embodiment having two sensors, for example, a single Weighting Coefficient (COEFF) is used according to Equation 1 hereinabove described and repeated below for convenience of the reader as follows: $OPR = [(1-COEFF)*SPR_{act}] + (COEFF*SPR_{press})$. Thus, a simple means for adjusting the weight multipler or "sensor coefficient" for each Sensor Pacing Rate (SPR) is provided, wherein the weight $SPR_{act}$ is given varies inversely with respect to the weight $SPR_{press}$ is given, as the COEFF is adjusted. Thus, for any COEFF value ranging from 0 to 1, the equivalent "sensor coefficient" for each SPR is as follows:

| SPR type | "sensor coefficient" value |
| --- | --- |
| $SPR_{act}$ | value = (1 − COEFF) |
| $SPR_{press}$ | value = COEFF |

Therefore, making an adjustment in the COEFF such that a particular selected or favored sensor's SPR will be given greater weight or emphasis than the other sensor's SPR (i.e., the selected sensor's "sensor coefficient" will be increased and the other sensor's "sensor coefficient" will be decreased) is characterized as "shifting the COEFF toward the favored sensor". In the preferred embodiment, for example, "shifting the COEFF toward the favored sensor" requires the following adjustment in the COEFF:

| Favored Sensor (SPR type) | COEFF Adjustment |
| --- | --- |
| $S_1$ ($SPR_{act}$) | Decrement COEFF |
| $S_2$ ($SPR_{press}$) | Increment COEFF. |

Consequently, a COEFF value of 0 will most heavily favor the weighting for $S_1$ ($COEFF_{S1}$), and a COEFF value of 1.0 will most heavily favor the weighting for $S_2$ ($COEFF_{S2}$).

(12) An Optimization Flag (OPT.FLAG) corresponding to each sensor (e.g., $OPT.FLAG_{act}$ and $OPT.FLAG_{press}$) is used to provide an indication of optimization activity taken with respect to sensor gain optimization for each sensor. OPT.FLAG can be set to three different values (e.g., 1, 2 or 3) which correspond to three conditions ("OK", "ADJUSTED" or "STUCK") identifying the type of optimization activity taken:

| Condition | Optimization Activity |
|---|---|
| "OK" | Gain adjustment not needed and not made (since ACT.COUNT is within OPT.RANGE). |
| "ADJUSTED" | Gain was adjusted by increment or decrement (required since ACT.COUNT is outside of OPT.RANGE). |
| "STUCK" | Gain adjustment was needed but could not be made (although ACT.COUNT was outside of OPT.RANGE, sensor gain was locked high or locked low). |

B. Rules for Sensor Gain Optimization (1) If a sensor is within range, its sensor gain will not be adjusted.

(2) If a sensor is overachieving and its gain is not at minimum gain, its gain will be decreased one setting.

(3) If a sensor is underachieving and its gain is not at maximum gain, its gain will be increased one setting.

(4) Gain for both sensors can be changed each optimization cycle if conditions B(2) or B(3) exist.

(5) If a sensor is overachieving and its sensor gain is already set at minimum (i.e. stuck in a locked low condition), then its sensor gain cannot be decreased further, and no sensor gain adjustment will be made.

(6) If a sensor is underachieving and its gain is already set at maximum gain (i.e., stuck in a locked high condition), then its sensor gain cannot be increased further, and no sensor gain adjustment will be made.

C. Rules for Sensor Weighting Optimization (1) If a sensor's gain is adjusted in an optimization cycle, no adjustment in that sensor's "sensor coefficient" will be made during that optimization cycle (i.e., no adjustment to the COEFF value will be made during that cycle). Thus, in the preferred embodiment, when only one sensor's gain is adjusted, regardless of the gain optimization activity for the other sensor, no adjustment in weighting will be performed during that cycle.

(2) If both sensor gains are adjusted in an optimization cycle, no adjustment in weighting will be made during that optimization cycle (i.e., no adjustment to the COEFF value will be made during that cycle).

(3) If both sensors are within range (i.e., achieving their criteria), regardless of their gain settings, the weighting coefficient is adjusted one setting from its current COEFF value (i.e., a single step increment or decrement of 0.125) toward the Programmed Coefficient Value ($COEFF_{PROG}$).

(4) If both sensors are underachieving and both sensor gains are already set at maximum gain (i.e., both sensor gains are stuck in a locked high condition), the COEFF is shifted from its current value to the $COEFF_{PROG}$ in a single adjustment.

(5) If both sensors are overachieving and both sensor gains are already set at minimum gain (i.e., both sensor gains are stuck in a locked low condition), the COEFF is shifted from its current value to the $COEFF_{PROG}$ in a single adjustment.

(6) If one of the sensors is overachieving and its sensor gain is already set at minimum gain (i.e., its sensor gain is stuck in a locked low condition), and the other sensor is underachieving and its sensor gain is already set at maximum gain (i.e., its sensor gain is stuck in a locked high condition), the COEFF is shifted from its current value to the $COEFF_{PROG}$ in a single adjustment.

(7) If one of the sensors is underachieving and its sensor gain is set at maximum (i.e., its sensor gain is stuck in a locked high condition) and the other sensor is within range, then the sensor which is within range is be characterized as the "favored sensor" and the other sensor whose sensor gain is stuck is characterized as the "stuck sensor". In this situation, the COEFF is adjusted one setting from its current COEFF value (i.e., a single step increment or decrement of 0.125), by "shifting toward the favored sensor" (i.e., the favored sensor's SPR will be given greater weight or emphasis than the stuck sensor's SPR).

(8) If one of the sensors is overachieving and its sensor gain is set at minimum (i.e., its sensor gain is stuck in a locked low condition) and the other sensor is within range, then the sensor which is within range is be characterized as the "favored sensor" and the other sensor whose sensor gain is stuck is characterized as the "stuck sensor". In this situation, the COEFF is adjusted one setting from its current COEFF value (i.e., a single step increment or decrement of 0.125), by "shifting toward the favored sensor" (i.e., the favored sensor's SPR will be given greater weight or emphasis than the stuck sensor's SPR).

FIG. 4 illustrates the basic function of software for performing optimization of sensor gain, according to the present invention. For ease of explanation, sensor gain optimization logic is shown for one sensor only, using the activity (first) sensor $S_1$ for this example. It will be understood, however, that the software logic described in FIG. 4 is applicable to pacemakers having one, two, or more sensors, for which an optimization of sensor rate response or gain as a function of an Achievement Criterion is desired, and the logic is essentially identical for each sensor gain being optimized (e.g., for optimizing PRESS.GAIN for the second sensor $S_2$).

Entering the flowchart at starting position B, a determination is made at composite block, shown by dashed line at 400, as to whether the sensor's Achievement Count ($ACH.COUNT_{act}$) is "within range" of its Optimization Range ($OPT.RANGE_{act}$), namely, whether $OPT.RANGE.MIN_{act} \geq ACH.COUNT._{act} \leq OPT.RANGE.MAX_{act}$. A determination that $ACH.COUNT_{act}$ was "within range" for the twenty-four hour Optimization Period (OPT.PERIOD) which has just elapsed in indicative in that the sensor's gain (ACT.GAIN) or rate response setting (RR) was appropriate for the patient's needs, and no sensor gain adjustment is necessary for gain optimization.

A determination is first made at block 400A as to whether the activity sensor was underachieving, namely, whether its Achievement Count is below its Optimization Range (i.e., whether $ACT.COUNT_{act} < OPT.RANGE.MIN_{act}$). A decision of NO at block 400A results if the sensor was not underachieving (i.e., $ACT.GAIN \geq OPT.RANGE.MIN_{act}$). Consequently, a determination is then made at block 400B as to whether the activity was overachieving, namely, whether its Achievement Count is above its Optimization Range (i.e., whether $ACT.COUNT_{act} > OPT.RANGE.MAX_{act}$). A decision of NO at block 400B results if the sensor was not overachieving (i.e., $ACT.GAIN \leq OPT.RANGE.MAX_{act}$). Under these conditions, no sensor gain adjustment is required, and the Optimization Flag (OPT.FLAG$_{act}$) is set at block 402 to "OK" status, followed by exiting this flowchart at exit position C to commence the sensor weighting optimization logic shown in FIG. 5.

A determination, however, at composite block 400 that the sensor's Achievement Count (ACH.COUNT$_{act}$) is not "within range" of its Optimization Range (OPT.RANGE$_{act}$) being used for the Optimization Period (OPT.PERIOD) which has just elapsed (i.e., the sensor was either underachieving or overachieving), will cause pacemaker 100 to perform the remainder of optimization logic shown in FIG. 4.

A determination that the Achievement Count is not "within range" indicates that the sensor gain was not set to optimally meet the needs of the patient over the previous Optimization Period which has just elapsed (i.e., ACT.GAIN should be incremented or decremented for the next Optimization Period, since sensor $S_1$ was either overachieving or underachieving its Achievement Criterion). The objective, therefore, of this optimization logic will be to cause, if possible, an adjustment to be made to the sensor gain (increment or decrement).

The gain adjustment will be made by pacemaker 100 in such a manner that the sensor's Achievement Count developed during the next Optimization Period will be more likely fall "within range" of its Optimization Range. Consequently, the activity-driven, rate response behavior of pacemaker 100 will be optimized as a function of the Achievement Criterion for the activity sensor.

Returning to composite block 400, a decision of YES results at block 400A if sensor $S_1$ was underachieving (i.e., ACT.COUNT$_{act}$ <OPT.RANGE.MIN$_{act}$). To provide a desired gain optimization in response to such detected underachievement, a determination is then made at block 404 as to whether the sensor gain (ACT.GAIN) is "stuck", or alternatively, whether it can be increased. A decision of NO results at block 404 if the current gain setting is not already set at its highest available sensor gain or rate response setting (i.e., NO if ACT.GAIN is not stuck in locked high condition which corresponds to the "maximum gain" of RR10 as shown in FIG. 6A in the preferred embodiment). Consequently, the sensor gain will be incremented one setting (e.g., from RR5 to RR6) at block 406, and the Optimization Flag (OPT.GAIN$_{act}$) is set at block 408 to "ADJUSTED" status, followed by exiting this flowchart at exit position C to commence the sensor weighting optimization logic shown in FIG. 5.

Conversely, a decision of YES results at block 404 if the current gain setting is already set at its highest available sensor gain or rate response setting (i.e., YES if ACT.GAIN=RR10). Therefore, ACT.GAIN is locked high and no further increase in sensor gain can be performed. Consequently, the Optimization Flag (OPT.GAIN$_{act}$) is set at block 410 to "STUCK" status, followed by exiting this flowchart at exit position C to commence the sensor weighting optimization logic shown in FIG. 5.

Returning again to composite block 400, a decision of YES results at block 400B if sensor $S_1$ was overachieving (i.e., ACT.COUNT$_{act}$>OPT.RANGE.MAX$_{act}$). To provide a desired gain optimization in response to such detected overachievement, a determination is then made at block 412 as to whether the sensor gain (ACT.GAIN) is "stuck", or alternatively, whether it can be decreased. A decision of NO results at block 412 if the current gain setting is not already set at its lowest available sensor gain or rate response setting (i.e., NO if ACT.GAIN is not stuck in locked low condition which corresponds to the "minimum gain" of RR1 as shown in FIG. 6A in the preferred embodiment). Consequently, the sensor gain will be decremented one setting (e.g., from RR5 to RR4) at block 414, and the Optimization Flag (OPT.GAIN$_{act}$) is set at block 416 to "ADJUSTED" status, followed by exiting this flowchart at exit position C to commence the sensor weighting optimization logic shown in FIG. 5.

Conversely, a decision of YES results at block 412 if the current gain setting is already set at its lowest available sensor gain or rate response setting (i.e., YES if ACT.GAIN=RR1). Therefore, ACT.GAIN is locked low and no further decrease in sensor gain can be performed. Consequently, the Optimization Flag (OPT.GAIN$_{act}$) is set at block 418 to "STUCK" status, followed by exiting this flowchart at exit position C to commence the sensor weighting optimization logic shown in FIG. 5.

It will be understood that the same sensor gain optimization logic shown in FIG. 4 will also be performed for the second sensor $S_2$, commencing at starting position B and concluding at exit position C, to provide the appropriate adjustment, if possible, to the pressure sensor's gain (PRESS.ACT).

FIG. 5 illustrates the basic function of software for performing optimization of sensor Weighting Coefficient (COEFF), according to the present invention. At the end of each Optimization Period, following the sensor gain optimization procedure described in FIG. 4, the sensor weighting optimization procedure will be performed. The objective of this optimization logic will be to cause, if possible, the Weighting Coefficient to be varied as function of the rate response or gain adjustments which were made, if possible, for each sensor during the sensor gain optimization procedure. Thus, the Weighting Coefficient (COEFF) is varied as a function of the Achievement Criterion for each of the sensors, such that the proportion or weight of control given to each sensor's output is regulated appropriately for purposes of deriving an Optimized Pacing Rate for the patient.

Upon entering the flowchart at starting position C, the Optimization Flag for activity sensor $S_1$ (OPT.FLAG$_{act}$) and the Optimization Flag for pressure sensor $S_2$ (OPT.FLAG$_{press}$) will have been set to their respective values which correspond to the optimization activity performed during the sensor gain optimization cycle described in FIG. 4 (e.g., OPT.FLAG="OK", "ADJUSTED" or "STUCK"). Adjustments made in the sensor weighting optimization procedure will be made based upon the respective values for each of these Optimization Flags, according to the logic rules hereinabove described in Part VI.

A determination is made at block 500 as to whether the gain for $S_1$ was adjusted. A decision of YES at block 500 results if the first sensor's rate response (ACT.GAIN) was adjusted (i.e., Yes if OPT.FLAG$_{act}$="ADJUSTED"). At this point, therefore, OPT.FLAG$_{act}$="ADJUSTED", and OPT.FLAG$_{press}$ corresponds to either "OK", "ADJUSTED" or "STUCK". Under this condition, no adjustment to the Weighting Coefficient is necessary. Before exiting this flowchart at exit position D to commence another Optimization Period, however, the various registers associated with providing the flagging, counting and timing functions for the sensor gain and sensor weighting optimization procedures, such as for setting the Optimization Flags and timing the Optimization Period, are reset to the appropriate starting values at block 502.

A decision of NO at block 500 results if the first sensor's rate response (ACT.GAIN) was not adjusted during the sensor gain optimization procedure. At this point, therefore, OPT.FLAG$_{act}$ corresponds to either "OK" or "STUCK", and OPT.FLAG$_{press}$ corresponds to either "OK", "ADJUSTED" or "STUCK".

A determination is then made at block 504 as to whether the gain for $S_2$ was adjusted. A decision of YES at block 504 results if the second sensor's rate response (PRESS.GAIN) was adjusted (i.e., Yes if OPT.FLAG$_{press}$="ADJUSTED"). At this point, therefore, OPT.FLAG$_{act}$ corresponds to either "OK" or "STUCK", and OPT.FLAG$_{press}$="ADJUSTED". Under this condition, no adjustment to the Weighting Coefficient is necessary. Therefore, appropriate resetting functions at block 502 are performed, followed by exiting this flowchart at exit position D to commence another Optimization Period.

A decision of NO at block 504 results if the second sensor's rate response (PRESS.GAIN) was not adjusted during the sensor gain optimization procedure. At this point, therefore, OPT.FLAG$_{act}$ corresponds to either "OK" or "STUCK", and OPT.FLAG$_{press}$ corresponds to either "OK" or "STUCK".

A determination is then made at block 506 as to which of the two remaining situations account for the absence of a gain adjustment for $S_1$, namely, whether OPT.FLAG$_{act}$ corresponds to "OK" or "STUCK". The specific test used is whether OPT.FLAG$_{act}$ corresponds to "OK".

A decision of YES at block 506 results if the non-adjustment was due to the fact that $S_1$ was achieving its Achievement Criterion, namely, that its ACH.COUNT$_{act}$ was "within range" of its OPT.RANGE$_{act}$ (i.e., YES if OPT.FLAG$_{act}$ corresponds to "OK"). At this point, therefore, OPT.FLAG$_{act}$ corresponds to "OK", and OPT.FLAG$_{press}$ corresponds to either "OK" or "STUCK".

Following a decision of YES at block 506, a determination is then made at block 508 as to which of the two remaining situations account for the absence of a gain adjustment for $S_2$, namely, whether OPT.FLAG$_{press}$ corresponds to "OK" or "STUCK". The specific test used is whether OPT.FLAG$_{press}$ corresponds to "OK".

A decision of YES at block 508 results if the non-adjustment was due to the fact that $S_2$ was achieving its Achievement Criterion, namely, that its ACH.COUNT$_{press}$ was "within range" of its OPT.RANGE$_{press}$ (i.e., YES if OPT.FLAG$_{press}$ corresponds to "OK"). At this point, therefore, OPT.FLAG$_{act}$ and OPT.FLAG$_{press}$ both correspond to "OK". Under this condition, it is desirable to adjust the current COEFF value toward the COEFF$_{PROG}$ in a single step increment or decrement of 0.125. A determination is first made at block 510 as to whether the Weighting Coefficient (COEFF) is already set at its Programmed Coefficient Value (COEFF$_{PROG}$).

If a decision of YES at block 510 results, no adjustment to COEFF is necessary. Therefore, appropriate resetting functions at block 502 are performed, followed by exiting this flowchart at exit position D to commence another Optimization Period. A decision of NO at block 510 requires the current COEFF value be adjusted at block 512 toward the COEFF$_{PROG}$ in a single step increment or decrement of 0.125, followed by resetting functions at block 502 and exiting at D to commence another Optimization Period.

Returning again to block 508, a decision of NO results at block 508 if the non-adjustment was due to the fact that $S_2$ was failing to achieve its Achievement Criterion and its desired gain adjustment could not be made because it was stuck in locked high condition (i.e., RR10 while underachieving) or it was stuck in locked low condition (i.e., RR1 while overachieving) (i.e., NO if OPT.FLAG$_{press}$ corresponds to "STUCK"). At this point, therefore, OPT.FLAG$_{act}$ corresponds to "OK", and OPT.FLAG$_{press}$ corresponds to "STUCK".

In this situation, $S_1$ is considered the "favored sensor" and $S_2$ is considered the "stuck sensor". Under this condition, it is desirable to shift the COEFF toward the favored sensor, such that the Sensor Pacing Rate for the favored sensor (SPR$_{act}$) is given greater weight or emphasis than that of the stuck sensor (SPR$_{press}$) for purposes of deriving the Optimized Pacing Rate (OPR) according to Equation 1 hereinabove set forth in Part II. This is accomplished by shifting from the current COEFF value toward a COEFF value which will most heavily favor the weighting for $S_1$.

In the preferred embodiment, the limit to which COEFF can be shifted to most heavily weight SPR$_{act}$ is a COEFF setting of 0 (such limit referred to as COEFF$_{S1}$). A determination is first made at block 514, therefore, as to whether the COEFF is already set at COEFF$_{S1}$. If a decision of YES at block 514 results, no adjustment to COEFF is necessary. Therefore, appropriate resetting functions at block 502 are performed, followed by exiting this flowchart at exit position D to commence another Optimization Period. If a decision of NO at block 514 results, the current COEFF value is adjusted at block 516 toward the favored sensor (i.e., adjust the COEFF value toward its limit of COEFF$_{S1}$) in a single step decrement of 0.125, followed by resetting functions at block 502 and exiting at D to commence another Optimization Period.

Returning again to block 506, a decision of NO at block 506 results if the non-adjustment was due to the fact that $S_1$ was failing to achieve its Achievement Criterion and its desired gain adjustment could not be made because it was stuck in locked high condition (i.e., RR10 while underachieving) or it was stuck in locked low condition (i.e., RR1 while overachieving) (i.e., NO if OPT.FLAG$_{act}$ corresponds to "STUCK"). At this point, therefore, OPT.FLAG$_{act}$ corresponds to "STUCK", and OPT.FLAG$_{press}$ corresponds to either "OK" or "STUCK".

Following a decision of NO at block 506, a determination is then made at block 518 as to which of the two remaining situations account for the absence of a gain adjustment for $S_2$, namely, whether OPT.FLAG$_{press}$ corresponds to "OK" or "STUCK". The specific test used is whether OPT.FLAG$_{press}$ corresponds to "OK".

A decision of YES at block 518 results if the non-adjustment was due to the fact that $S_2$ was achieving its Achievement Criterion, namely, that its ACH.COUNT$_{press}$ was "within range" of its OPT.RANGE$_{press}$ (i.e., YES if OPT.FLAG$_{press}$ corresponds to "OK"). At this point, therefore, OPT.FLAG$_{act}$ corresponds to "STUCK", and OPT.FLAG$_{press}$ corresponds to "OK". In this situation, $S_2$ is considered the "favored sensor" and $S_1$ is considered the "stuck sensor".

Under this condition, it is desirable to shift the COEFF toward the favored sensor, such that the Sensor Pacing Rate for the favored sensor ($SPR_{press}$) is given greater weight or emphasis than that of the stuck sensor ($SPR_{act}$) for purposes of deriving the Optimized Pacing Rate (OPR) according to Equation 1 hereinabove set forth in Part II. This is accomplished by shifting from the current COEFF value toward a COEFF value which will most heavily favor the weighting for $S_2$. In the preferred embodiment, the limit to which COEFF can be shifted to most heavily weight $SPR_{press}$ is a COEFF setting of 1.0 (such limit referred to as $COEFF_{S2}$). A determination is first made at block 520, therefore, as to whether the COEFF is already set at $COEFF_{S2}$.

If a decision of YES at block 520 results, no adjustment to COEFF is necessary. Therefore, appropriate resetting functions at block 502 are performed, followed by exiting this flowchart at exit position D to commence another Optimization Period. If a decision of NO at block 520 results, the current COEFF value is adjusted at block 522 toward the favored sensor (i.e., adjust the COEFF value toward its limit of $COEFF_{S1}$) in a single step increment of 0.125, followed by resetting functions at block 502 and exiting at D to commence another Optimization Period.

Returning again to block 518, a decision of NO at block 518 results if the non-adjustment was due to the fact that $S_2$ was failing to meet it Achievement Criterion and its desired gain adjustment could not be made because it was stuck in locked high condition (i.e., RR10 while underachieving) or it was stuck in locked low condition (i.e., RR1 while overachieving) (i.e., NO if $OPT.FLAG_{press}$ corresponds to "STUCK"). At this point, therefore, $OPT.FLAG_{act}$ and $OPT.FLAG_{press}$ both correspond to "STUCK". Under this condition, it is desirable to adjust the COEFF from its current value to the $COEFF_{PROG}$ in a single adjustment.

For example, if $COEFF_{PROG}$ is programmed at 0.500 and the current value of COEFF is 0.750, then a single adjustment decrementing COEFF by 0.250 to the programmed value of 0.500 would be made. A determination is first made at block 524 as to whether the current value of the Weighting Coefficient (COEFF) is already set at its Programmed Coefficient Value ($COEFF_{PROG}$). If a decision of YES at block 524 results, no adjustment to COEFF is necessary. Therefore, appropriate resetting functions at block 502 are performed, followed by exiting this flowchart at exit position D to commence another Optimization Period. A decision of NO at block 524 requires the current COEFF value be adjusted at block 526 from it current COEFF value to the $COEFF_{PROG}$ in a single adjustment, followed by resetting functions at block 502 and exiting at D to commence another Optimization Period.

Thus, it can be appreciated that the present invention provides a very flexible means for optimization of rate responsiveness in a pacemaker, while offering simplicity of implementation. It will be apparent to those skilled in the art, for example, that the sensor gain optimization procedure can be practiced separately from the sensor weighting optimization procedure, each of which can be varied as a function of their own selected achievement criterion.

The self-adapting rate optimization behavior provided by the optimization procedures of the present invention are believed, for example, to minimize most difficulties ordinarily associated with combining sensors which sense different rate control parameters, such difficulties including differences in (1) long-term stability; (2) immunity to noise; (3) response time to changing metabolic conditions; and (5) correlation between sensor output and the rate control parameter being measured (i.e., variations in linearity). Consequently, the present invention introduces greater freedom of choice to the clinician with respect to the types of sensors which may be used therewith.

Selecting rate control parameters which have highly complementary characterisitcs is not necessarily required. In fact, the present invention can be practiced, for example, with sensors having less rapid onset of detected metabolic change than those described herein. Other sensor combinations might include, for example, one sensor to determine timing and the other the magnitude of response. As another example, sensors having maximum sensitivity at different levels of exertion might be used.

Figure 7:
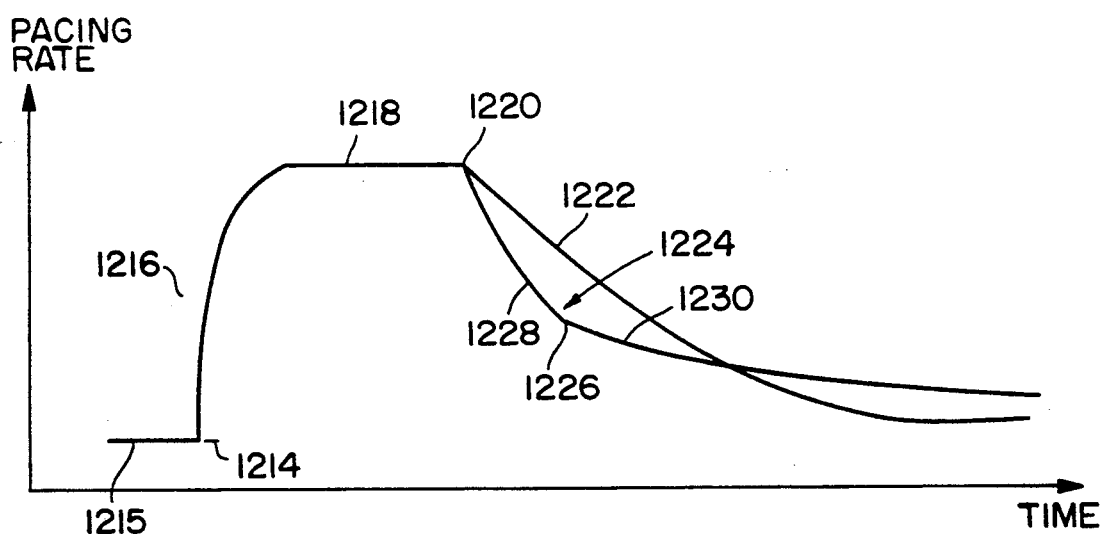
FIG. 7 is a graph illustrating the modified decay curve of the pacemaker of FIG. 1, in comparison to the behavior of a conventional pacemaker.

The distinction between the behavior of a pacemaker employing the present invention and one according to the prior art is best understood by consideration of FIG. 7. FIG. 7 illustrates a pacing rate curve in a conventional activity sensing rate responsive pacemaker as compared to a normal heart decay curve. The vertical axis represents the pacing rate in pulses per minute (ppm), and the horizontal axis represents time in seconds.

Turning now to FIG. 7, the modified decay feature of the pacemaker 100 will now be described. The patient is initially at rest, as indicated by line 1,212, and the pacemaker is pacing at a predetermined lower rate. The deflection point 1,214 indicates that the patient has started to increase his or her activity level, and the attack or acceleration curve 1,216 shows the pacemaker responding to such increased activity level.

When the attack curve reaches a plateau 1,218, the pacing rate generally stabilizes at an activity determined rate or an upper rate for the duration of the exercise or physical activity. A deflection point 1,220 indicates that the patient's activity level has ceased or has been reduced substantially, and that the pacemaker is now ready to decelerate the pacing rate.

Two decay or deceleration curves 1,222 and 1,224 descend from the deflection point 1,220 and indicate a decrease in the patient's activity level. In the absence of intervening heightened activities, these two curves 1,222 and 1,224 tend to approach a predetermined pacing rate, such as the lower rate.

The decay curve 1,222 represents the deceleration curve in a conventional pacemaker, as exemplified in U.S. Pat. No. 4,722,342 issued to Amundson. The decay curve 1,224 on the other hand, represents the heart's normal deceleration rate, as illustrated in a textbook by Myrvin H. Ellestad, M.D., entitled "Stress Testing Principles and Practice", pages 489–492.

It is apparent that the curves 1,222 and 1,224 do not match completely, in that conventional pacemakers pace at an elevated rate, i.e. curve 1,222, with respect to the typical human response, i.e. curve 1,228, and thereafter return to the resting or lower rate sooner than the typical human response 1,230. This elevated pacing rate in conventional pacemakers may cause a sensation of the heart rate "racing" or beating too fast at the end of activity, perhaps even provoking a syncopal episode. Additionally, conventional pacemakers may pace too slowly for several minutes after the end of activity.

The curve 1,224 comprises two decay portions, an initial portion 1,228 and a latent portion 1,230, each decaying at a different time constant. As will be further explained in more details with respect to FIGS. 8 and 4, the selection of the switch point 1,226 and time constants of the initial and latent decay portions 1,228 and 1,230 is an important part of the invention.

Figure 8:
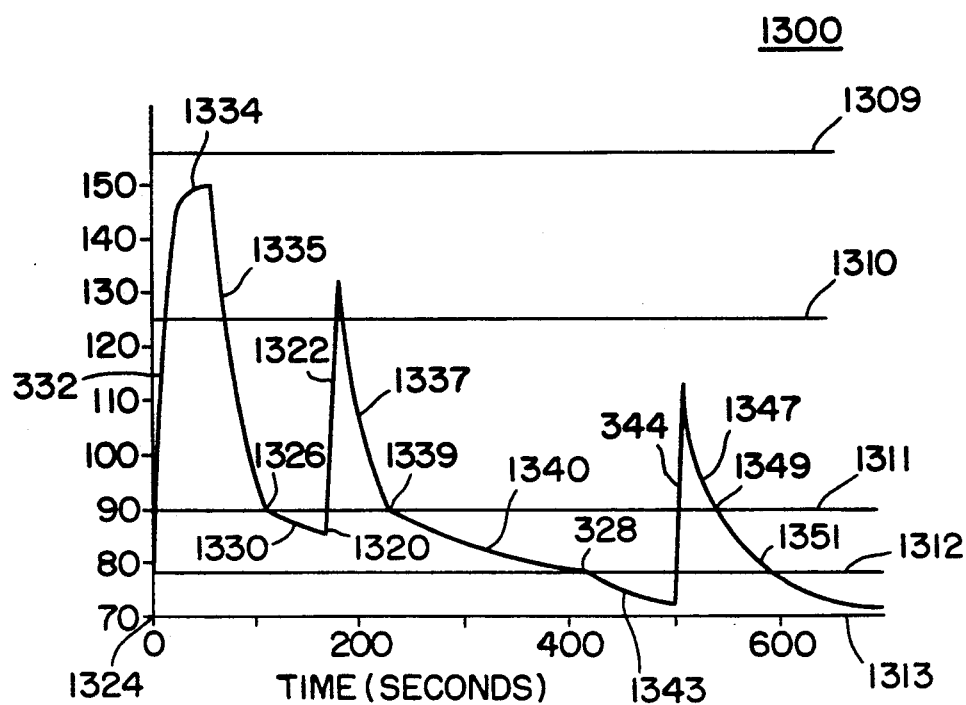
FIG. 8 is another graph further illustrating the behavior of the pacemaker of FIG. 1 employing the present invention.
Figure 9:
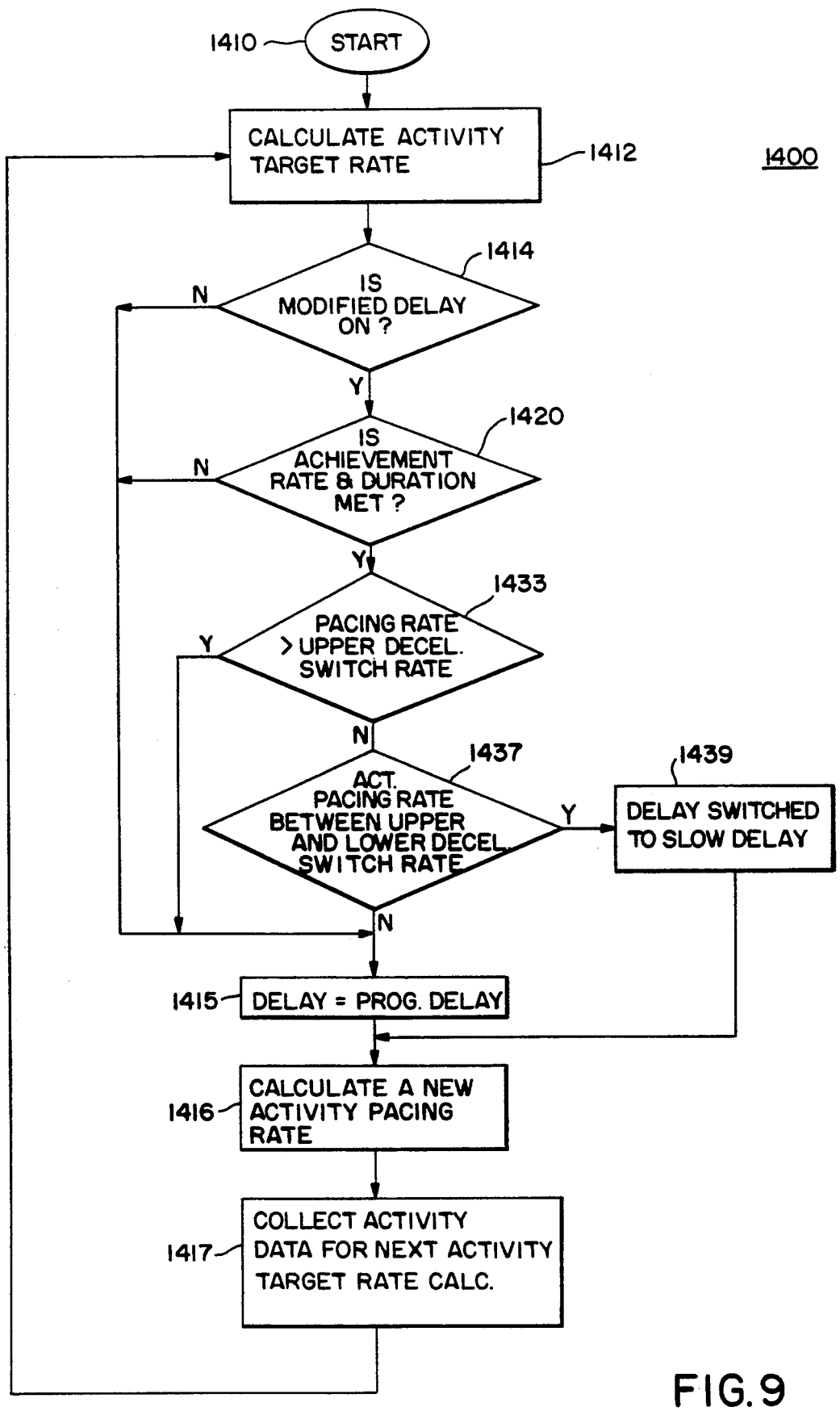
FIG. 9 is a flow chart illustrating the operation of the pacemaker of FIG. 1, according to the present invention.

The operation of the pacemaker 100 will now be described in greater details in relation to FIGS. 8 and 9. FIG. 8 illustrates an exemplary activity attack and decay curve 1,300 indicative of the behavior of the pacemaker 100, and FIG. 9 illustrates a simplified flow chart of the software used to control the operation of the pacemaker 100 according to the present invention.

The vertical axis in FIG. 8 represents the pacing rate in pulses per minute (ppm) and the horizontal axis represents time in seconds. Five threshold levels are illustrated as horizontal lines: the upper rate 1,309; the achievement rate 1,310; the upper switch rate 1,311; the lower switch rate 1,312; and the lower rate 1,313.

As defined above, the upper rate 1,309 is a value supplied by the physician which limits the maximum stimulation rate when the activity reaches or exceeds a certain level. The pacemaker 100 is not allowed to pace above the upper rate 1,309. The achievement rate 1,310 is a value that can be set by the physician and represents a predetermined percentage of the difference between the upper rate 1,309 and the lower rate 1,313, as follows:

Achievement Rate = Lower Rate + $a$(Upper Rate − Lower Rate), where "a" is a percentile value which preferably ranges between 50% and 100%. The achievement rate 1,310 may vary from one patient to another. However, for illustration purposes, an exemplary achievement rate 1,310 is selected as 125 ppm.

The upper switch rate 1,311 is a value that can be selected by the physician and represents a predetermined percentage of the difference between the upper rate 1,309 and the lower rate 1,313, as follows:

Upper Switch Rate = Lower Rate + $u$(Upper Rate − Lower Rate), where "u" is a percentile value. The upper switch rate 1,311 varies from one patient to another. However, the preferred range for the upper switch rate 1,311 is between 20% and 50%. For illustration purposes, the upper switch rate 1,311 is chosen as 90 ppm.

This upper switch rate 1,311 is an important factor in the present invention in that it determines an upper switch point 1,326, which is graphically represented as the intersection point between the activity curve 1,300 and the upper switch rate 1,311. This upper switch point 1,326 corresponds to the switch point 1,226 in FIG. 7.

The lower switch rate 1,312 is a value which is also selected by the physician, and which represents a predetermined percentage of the lower rate 1,313, as follows:

Lower Switch Rate = Lower Rate + 10% Lower Rate.

For illustration purposes, the lower switch rate threshold 1,312 is chosen as 77 ppm.

The lower switch rate 1,312 is also an important factor in the present invention in that it determines a lower switch point 1,328, which is graphically represented as the intersection point between the activity decay curve 1,300 and the lower switch rate threshold 1,312.

The lower rate 1,313 is a value supplied by the physician which limits the minimum stimulation rate when the activity decreases to or is below a certain level. The pacemaker 100 is not allowed to pace below the lower rate 1,313. For illustration purposes, the lower rate 1,313 is chosen as 70 ppm. While the above upper rate 1,309, achievement rate 1,310, upper switch rate 1,311, lower switch rate 1,312 and lower rate 1,313 can be individually selected, their values can be set to default values to simplify programming procedures.

The operation of the pacemaker 100 will now be described in relation to the activity attack and decay curve 1,300 in FIG. 8. While the operation of the pacemaker 100 will be described in relation to a flow chart, it should be understood that the same or a similar operation can be accomplished using conventional hardware and integrated circuit technology. The initial point 1,324 indicates that the patient is in a resting position and that the pacemaker 100 is pacing at the lower rate 1,313. When the patient is stressed by exercise, the pacemaker 100 responds by increasing the pacing rate, as illustrated by the attack curve 1,332, until it reaches a maximum pacing rate or plateau 1,334, at which time, the pacing rate stabilizes for the duration of the stress. The pacing rate 1,334 may be limited by the upper rate 1,309.

If the patient maintains a heightened exercise level, and the pacemaker 100 has paced above the achievement rate 1,310 for a predetermined interval of time, such as 4 seconds or longer, then the pacemaker 100 automatically triggers the inventive modified decay feature, whereby the decay curve 1,335 is deflected at the upper and lower switch points 1,326 and 1,328, as it reaches the upper switch rate threshold 1,311 and the lower switch rate threshold 1,312 respectively. It should be understood that the waiting interval of 4 seconds could be varied for each patient, depending on age, gender and activities which the patient engages into. Nonetheless, the 4 second interval has been selected to substantially minimize false triggering by artifacts.

Thus, upon decrease of the activity level, the pacemaker 100 is allowed to pace at a decreasing rate, with a selectable decay time constant such as 45 seconds. However, once the pacing rate reaches the upper switch rate threshold 1,311, the decay time constant is increased in order to slow the drop in the patient's pacing rate. This modified decay feature simulates the heart's normal behavior under the circumstances, and causes the pacemaker 100 to respond optimally to the individual patient's cardiovascular needs.

The modified decay curve 1,330 generally corresponds to the latent decay portion 1,230 in FIG. 7. If, prior to reaching the lower switch rate threshold 1,312 the patient resumes a sudden heightened stress or exercise level, then, as indicated by the deflection point 1,320, the pacing rate increases correspondingly, as indicated by the attack curve 1,322. It should be noted that, at this stage, since the modified decay curve 1,330 has not reached the lower switch rate threshold 1,312, the modified decay feature is still enabled, and has not been turned off. The modified decay feature will be triggered off when the pacing rate drops below the lower switch rate threshold 1,312, along the curve 1,343, at which time, the modified decay feature will not be enabled until the achievement criteria have been met once again.

Therefore, as the pacing rate decay curve 1,337 reaches the upper switch rate threshold 1,311, a corresponding switch point 1,339 causes a change in the deceleration time constant. In this manner, the pacing rate is allowed to decay along the decay curve 1,337 at the time constant of 45 seconds, and upon reaching the upper switch point 1,339, the pacing rate follows the modified decay curve 1,340.

The decay time constant of the modified decay curves 1,330 and 1,340 are substantially similar, and can be selected from a range of 90 to 180 seconds, with a preferred setting of 180 seconds. It should however be understood to one skilled in the art after reviewing the present disclosure that the decay curves 1,330 and 1,340 can have different time constants, depending on the desired behavior of the pacemaker 100.

Thus, in this particular example, since the attack curve has reached and exceeded the achievement rate threshold 1,310, it might be desirable to set the time constant of the decay curve 1,340 at a value intermediate between the decay time constant of the curve 1,335, i.e. 45 seconds, and the modified time constant of the decay curve 1,330, i.e. 180 seconds. By analogy, the decay time constant of the curve 1,337 could also be selected to differ from the conventional decay time constant of the curve 1,335, i.e. 45 seconds.

As the curve 1,340 reaches the lower switch rate threshold 1,312, its decay time constant changes to a faster time constant 1,343, similar to the conventional time constant of 45 seconds. A different time constant can be selected.

Furthermore, in the preferred embodiment, upon reaching the lower switch point 1,328, the modified decay feature is turned off, such that, as long as the patient's exercise levels do not cause the pacing rate to reach or exceed the achievement rate 1,310 for a predetermined length of time, then the pacing rate is allowed to decay at nominal 45 seconds time constant.

This feature is illustrated by the attack curve 1,344 which falls short of reaching the achievement rate threshold 1,310, and the decay curve 1,347 is followed, even though the pacing rate decays below the upper switch rate 1,311 and the lower switch rate 1,312. Hence, as illustrated, the curve 1,347 is allowed to decay with a single non interrupted time constant, since it is presumed that under such circumstances the patient does not require additional time to recoup from the increased sudden stress. Therefore, no deflection is effected at the intersection points 1,349 and 1,351.

It should also be understood that the pacemaker 100 can be programmed so that the intersection points 1,349 and 1,351 can become switch points similar to the upper and lower switch points 1,339 and 1,328. In the alternative, the pacemaker 100 can be programmed to cause the curve 1,347 to decay at a time constant different from that of the decay curve 1,335. Such variations are anticipated by the present description, and, for brevity purposes, they will not be characterized in greater details.

Furthermore, it should also be understood to one skilled in the art that one or more additional upper and lower switch levels can be added between the achievement rate threshold 1,310 and the upper switch rate threshold 1,311, as well as between the upper switch rate 1,311 and the lower rate 1,313, in order to generate a more gradual deflection of the overall decay curve.

Turning now to FIG. 9, the operation of the pacemaker 100 will now be described in greater detail in connection with the flow chart 1,400. The software program and/or hardware starts at 1,410, and then determines, at 1,412, the new target rate, according to the following equation:

$$TR = \frac{(\text{Activity Count} + D)}{C} * (32768 * 60/328)$$

In the above equation, TR is the target rate calculated in response to the activity sensor and C and D are programmable variables that generate the shape of the rate response curves per FIG. 6A.

A more detailed description of the above calculations can be found in the co-pending application, Ser. No. 455,717, entitled "METHOD AND APPARATUS FOR IMPLEMENTING ACTIVITY SENSING IN A PULSE GENERATOR", filed on Dec. 22, 1989, which is incorporated herein by reference. Thus, as indicated at block 1,412, the pacemaker 100 periodically calculates the activity target rate TR, at a two-second interval, along the curve 1,300 of FIG. 8.

Next, the software determines at 1,414, whether the modified decay feature has been activated or programmed via a programmer such as Medtronic Model 9760. If the modified decay feature has not been activated, then the software sets, at 1,415, the decay rate to be equal to the programmed decay rate, i.e. 45 seconds time constant.

The pacemaker then calculates the next activity pacing rate at 1,416, and saves the activity related data, at 1,417, for use in calculating the new activity target rate at 1,412. The above routine is repeated until the modified decay feature is activated.

If the modified decay feature has been enabled at 1,414, then, as indicated by block 1,420, the software determines whether the achievement criterion has been met, i.e. whether the pacing rate is greater than or equal to the achievement rate 1,310, for a period of 4 seconds or longer. If the achievement criterion has not been met, then the software sets, at 1,415, the decay rate to be equal to the programmed decay rate, calculates the activity pacing rate at 1,416, saves the activity data at 1,417, and then calculates the new activity target rate at 1,412.

If on the other hand, the achievement criterion has been met, then, as illustrated by block 1,433, the software determines whether the current pacing rate is greater than the upper switch rate threshold 1,311. If it is, then, once again, the software sets, at 1,415, the decay rate to be equal to the programmed decay rate, calculates the activity pacing rate at 1,416, saves the activity data at 1,417, and calculates the new activity target rate at 1,412.

If the pacing rate is less than or equal to the upper switch rate 1,311, then the software determines, at 1,437, whether the pacing rate is between the upper switch rate 1,311 and the lower switch rate 1,312. If it is, then, as indicated by block 1,439, the software changes the decay rate to the modified or slower decay rate, as illustrated by the decay curves 1,330 and 1,340 in FIG. 8. The activity pacing rate is calculated at 1,416, the activity data is then saved at 1,417, and a new activity target rate is calculated at 1,412.

If the pacing rate is less than the lower switch rate 1,312 then as indicated by block 1,415, the software changes the decay rate to the programmed value.

Turning now to FIG. 2, there is illustrated a block circuit diagram 1,500 of the pacemaker 100 utilizing a microprocessor with on-board and off-board RAM/ROM memory and an activity sensor for adjusting the physiologic pacing rate as a function of the patient activity. The functional description of the circuit 1,500 is provided in detail in the co-pending application Ser. No. 549,568, entitled "METHOD AND APPARATUS FOR ACCESSING A NON-VOLATILE MEMORY", filed on Jul. 6, 1990, and having the same assignee as the present application, and is incorporated herein by reference.

Figure 10:
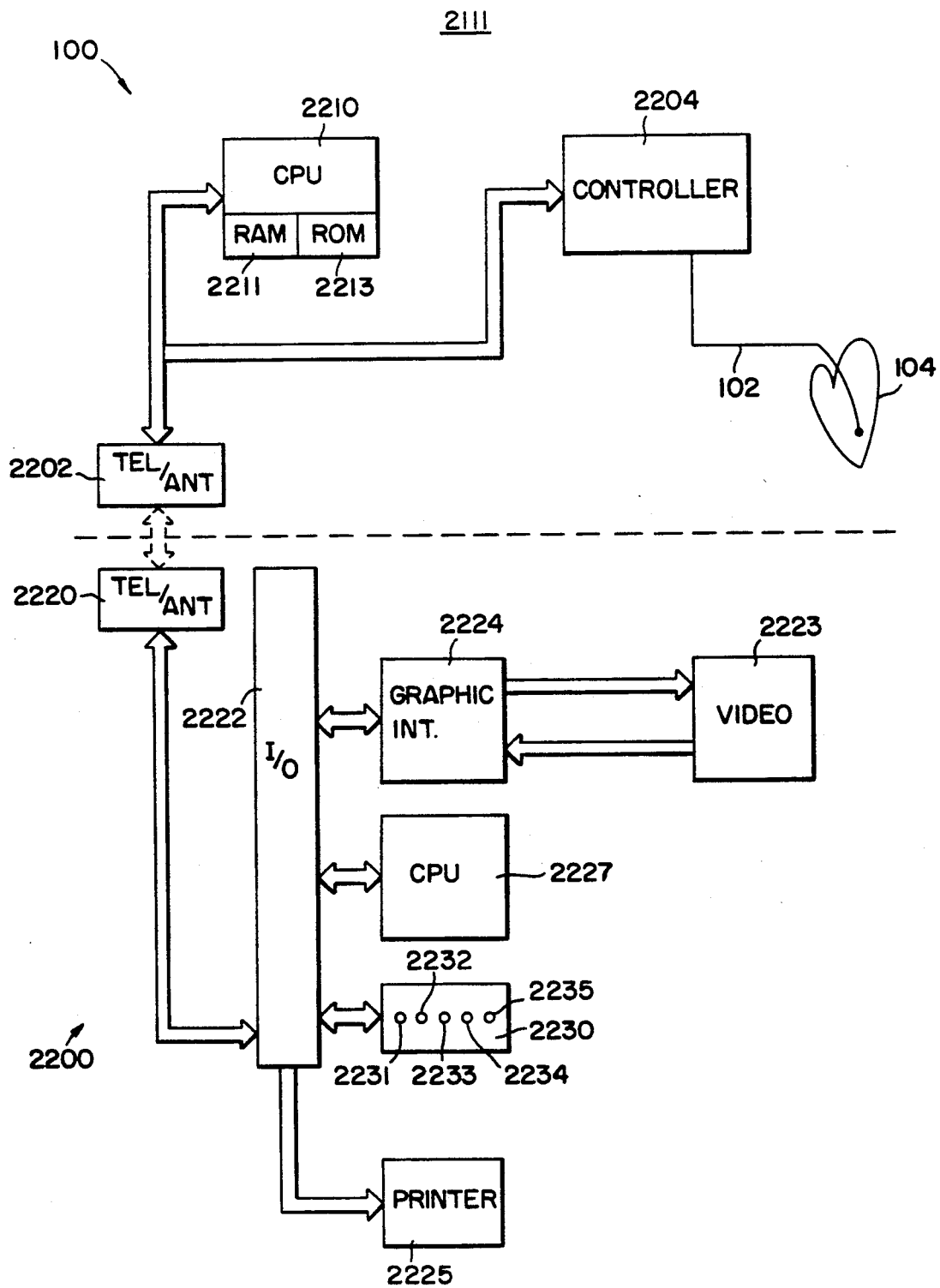
FIG. 10 is a system block diagram of a pacemaker system, illustrating the pacemaker of FIG. 1 in use with a programmer according to the present invention, to automatically initialize pacing parameters.

Turning now to FIG. 10, the automatic initialization feature of the pacemaker 100 will now be described in detail. FIG. 10 is a simplified system block diagram of a pacemaker system 2,111 and illustrates the pacemaker 100, in use with a programmer 2,200 according to the present invention. The programmer 2,200 uses a software program which allows the physician, among other applications, to reprogram or interrogate the pacemaker 100, and to cause the pacemaker 100 to uplink, via telemetry, measured values or logged data values to the programmer 2,200.

The hardware structure of the pacemaker system 2,111, i.e., the pacemaker 100 and the programmer 2,200 will now be described. The pacemaker 100 communicates with the programmer 2,200 over a telemetry port and antenna 2,202, and generally comprises a conventional multi-programmable system or controller 2,204. The multi-programmable system 2,204 contains conventional pacing and sensing functions known in the art.

A unipolar lead 102 with a pressure transducer interfaces between the multi-programmable system 2,204 and the heart 104.

The central processing unit (CPU) 2,210 includes random-access memory (RAM) 2,211 and read-only memory (ROM) 2,213 and manages desired function and stores temporary and programmed variables.

It should be noted that signal processing between the pacemaker 100 and the programmer 2,200 is accomplished in the manner described below in connection with FIGS. 11 through 15, and memories and data linkages are generated by suitable programming or software located in the programmer 2,200 memory or the memory of the pacemaker CPU 2,210.

Data transfer between the antenna/telemetry port 2,202 and the programmer 2,200 is effected via a programmer antenna/telemetry head 2,220, which, in turn, communicates with the corresponding telemetry input-/output (I/O) unit 2,222. The I/O unit 2,222 also interfaces with peripheral output equipment, such as a printer 2,225, and a video monitor 2,223 via a graphic display interface 2,224.

The programmer 2,200 includes its own central processing unit (CPU) 2,227 which interfaces with the I/O unit 2,222. The physician can, by means of the graphic display, view the data uplinked by the pacemaker 100 to the programmer 2,200, as well as the data to be downlinked to the pacemaker 100. The physician can enter or program the desired data or parameters using conventional means such as a keyboard, a light wand or other similarly available devices.

However, for simplicity purposes, the programmer 2,200 is described herein as having a control panel 2,230 with a series of control keys 2,231, 2,232, 2,233, 2,234 and 2.235. Other control and function keys are also available for various features, but are not shown in the drawings.

The general operation of the pacemaker 100 and the programmer 2,200 will now be described in relation to the pacemaker system 2,111 of FIG. 10, and the program 2,300 of FIG. 11. The physician starts the initialization process of the pacemaker 100 by placing the programmer antenna/ antenna/telemetry head 2,220 over the implant site of the pacemaker 100 in direct relation with the pacemaker antenna/telemetry port 2,202, for optimum data communication between the pacemaker 100 and the programmer 2,200, as indicated by block 2,301.

The physician has five options to initialize any or all of the following parameters: sensitivity threshold; pulse amplitude and width; activity threshold; and pressure (dP/dt) rate reponse gain. Each one of the control keys 2,231, 2,232, 2,233, 2,234 and 2,235 corresponds to an initialization function setting a flag to "true" as follows: Control key 2,231 corresponds to sensitivity threshold initialization; control key 2,232 corresponds to pulse amplitude and width initialization; control key 2,233 corresponds to activity threshold initialization; control key 2,234 corresponds to pressure initialization; and control key 2,235 corresponds to the initialization of all these above five parameters.

It should however be understood to those skilled in the art, after reviewing the present disclosure that other parameters, such as the refractory periods and rate response gain, can also be automatically initialized in a similar manner. The above five parameters have been selected as an example of the present automatic initialization feature. However, there is no intention to limit the present disclosure to these parameters.

Once the physician determines which parameter or parameters he or she wishes to initialize, then the physician presses the corresponding control key. If for instance, the physician wishes to have all the parameters initialized, he or she presses control key 2,235. In the alterative, control key 2,233 could be pressed for initializing the activity threshold parameter.

Figure 11:
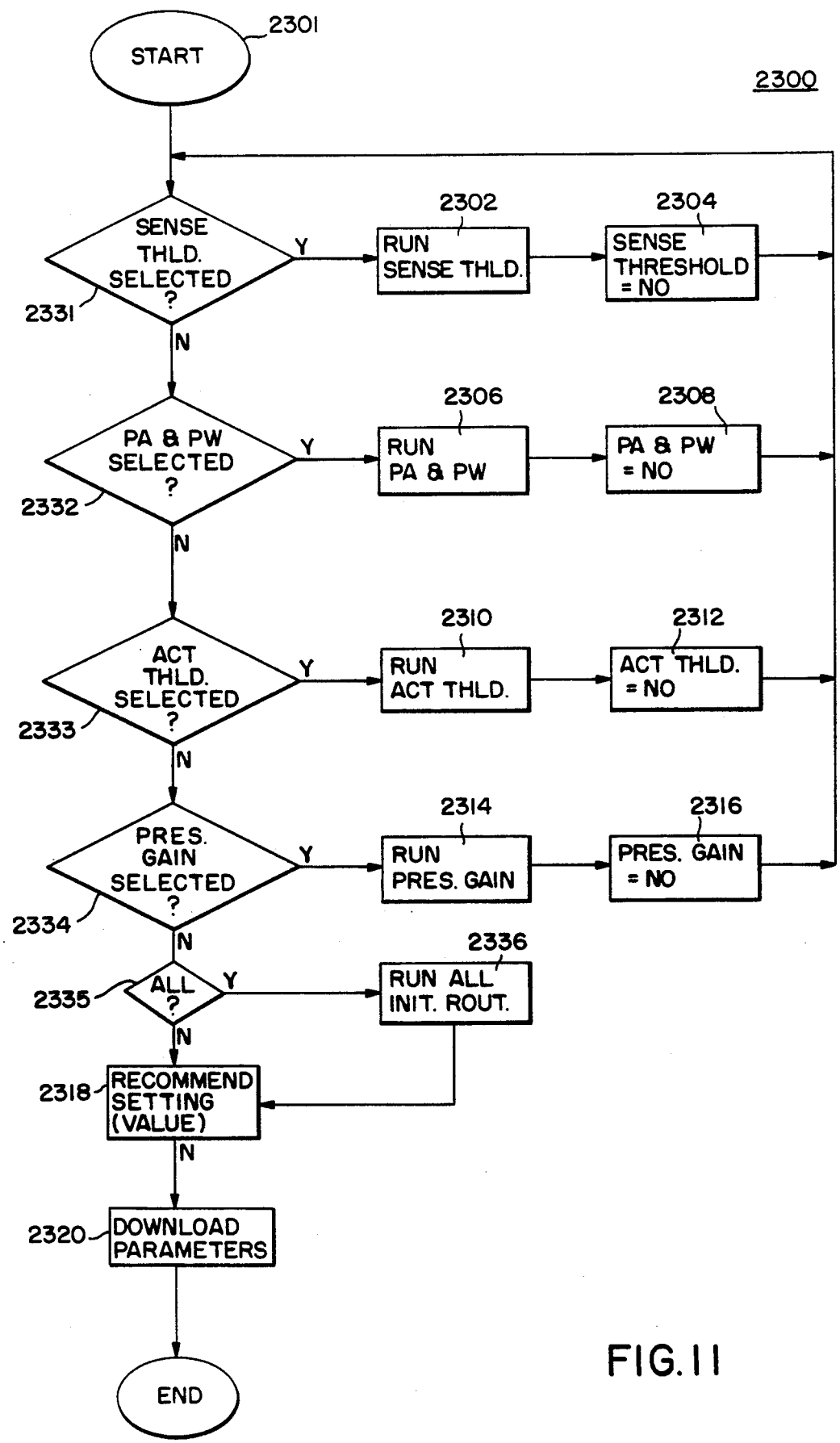
FIG. 11 is a flow chart illustrating the general method for initializing the pacemaker system of FIG. 10.

Turning now to FIG. 11, the software determines, at block 2,331, whether the operator or physician desires to have the sensitivity threshold parameter initialized. If it has, then, as indicated by block 2,302, the software runs the automatic initialization routine 2,400, which will be described later in greater details in connection with FIG. 12. Thereafter, the software program sets a "Sensitivity Threshold=False" flag, at 2,304, and the software once again inquires whether any other parameter needs to be automatically initialized.

If at block 2,331, the software determines that the sensitivity threshold parameter has not been selected, then the software inquires at 2,332, whether the pulse amplitude/width parameters have been selected for initialization. If they have, then, as indicated by block 2,306, the software runs the automatic initialization routine 2,500, which will be described later in greater details in connection with FIG. 13. Thereafter, the software program sets a "Pulse Amplitude/Width-=False" flag, at 2,308, and the software once again inquires whether any other parameter needs to be automatically initialized.

If at block 2,332, the software determines that the pulse width and amplitude parameters have not been selected, then the software inquires at 2,333, whether the activity threshold parameter has been selected for initialization. If it has, then, as indicated by block 2,310, the software runs the automatic initialization routine 2,600, which will be described later in greater details in connection with FIG. 14. Thereafter, the software program sets an "Activity Threshold=False" flag, at 2,312, and the software once again inquires whether any other parameter needs to be automatically initialized.

If at block 2,333, the software determines that the activity threshold parameter has not been selected, then the software inquires at 2,334, whether the pressure gain parameter has been selected for initialization. If it has, then, as indicated by block 2,314, the software runs the automatic initialization routine 2,700, which will be described later in greater details in connection with FIG. 15. Thereafter, the software program sets a "Pressure Gain=False" flag, at 2,316, and the software once again inquires whether any other parameter needs to be automatically initialized.

If at block 2,335, the software determined that all the parameters have been selected, then the surface runs all the initialization routines 2,400, 2,500, 2,600 and 2,700 and then recommends the preferred settings at 2,318.

If no other parameters have been selected for initialization, then, as indicated at 2,318, the initialized parameters are displayed on the monitor 2,223 as recommended optimal values. If the physician approves of such recommended values, then as indicated at 2,320, he or she simply presses a "Program" key (not shown), and the recommended values are downlinked to the pacemaker 100. In the alternative, the physician might selectively downlink the parameters he or she approves of, and reprogram or modify the remaining parameters in accordance with conventional practices.

While the preferred embodiment provides for the physician's precautionary check, it should be understood that the recommended parameters could, in the alternative, be downloaded without the physician's intervention.

Figure 12:
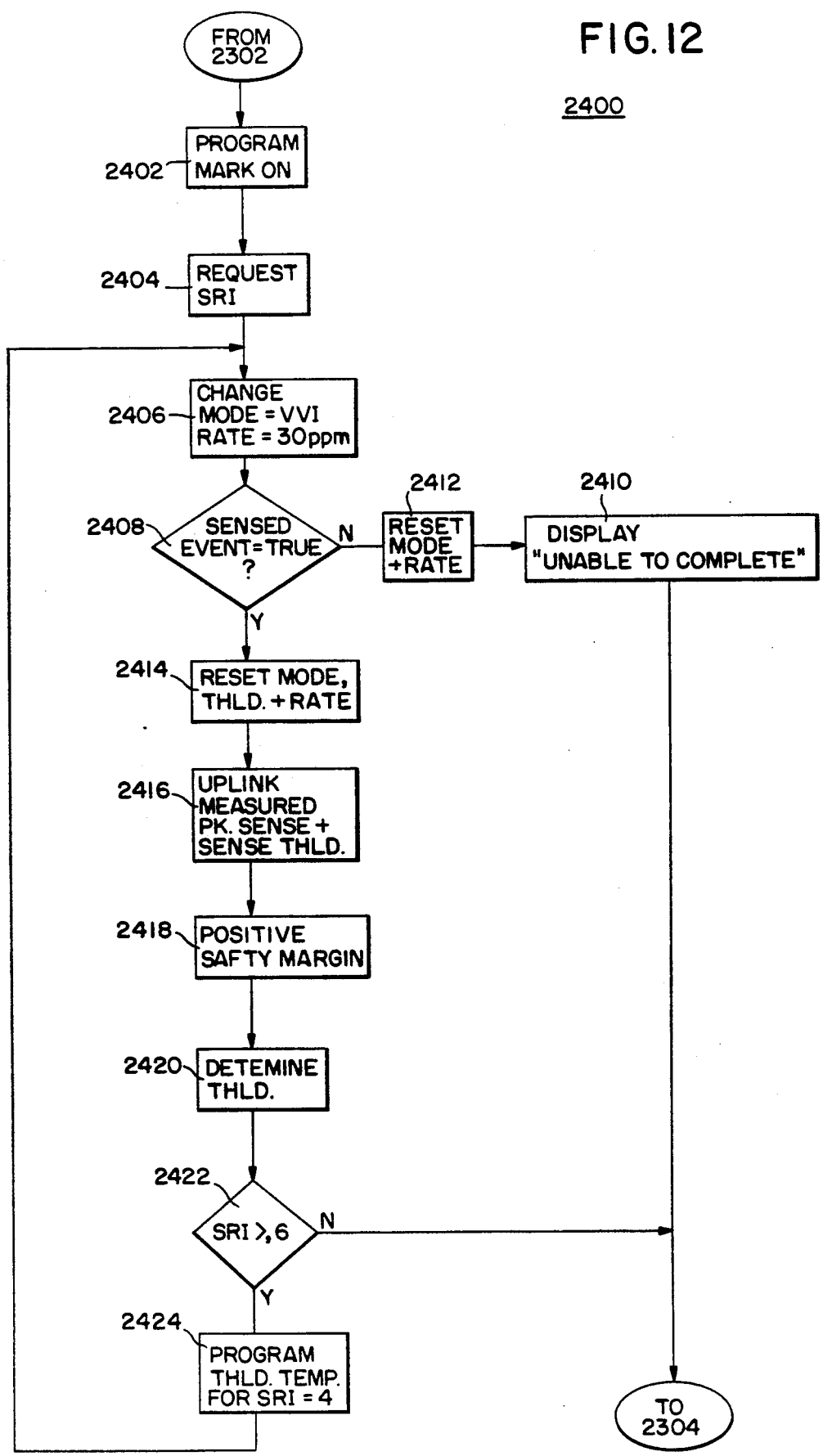
FIG. 12 is a simplified flow chart illustrating an automatic initialization routine for selecting the optimal sensitivity threshold according to the present invention.

Turning now to FIG. 12 of the drawings, there is illustrated, in a simplified flow chart format, the automatic initialization routine 2,400 for selecting the optimal sensitivity threshold. The purpose of this automatic initialization is to rapidly and accurately set the sense amplifier (not shown) threshold setting and to allow for an adequate margin of safety, in order to ensure that it is neither oversensing nor undersensing.

The software starts by enabling a marker channel at 2,402. As defined herein, the marker channel refers to a family of event-identifying codes which are telemetered to the programmer 2,200 to indicate the occurrence of specific events, such as sensed and paced events, in the pacemaker 100. A channel marker telemetry system is described in detail in U.S. Pat. No. 4,374,382, entitled "MARKER CHANNEL TELEMETRY SYSTEM FOR A MEDICAL DEVICE", issued to Markowitz, and assigned to the Medtronic, Inc. This patent is incorporated herein by reference. In a default transmission mode, or upon receiving the proper programming message, the pacemaker 100 transmits a marker code indicating the occurrence of sensing and pacing events in the heart. The marker channel includes a continuous transmission of idle frames until the event to be marked occurs.

Figure 12A:
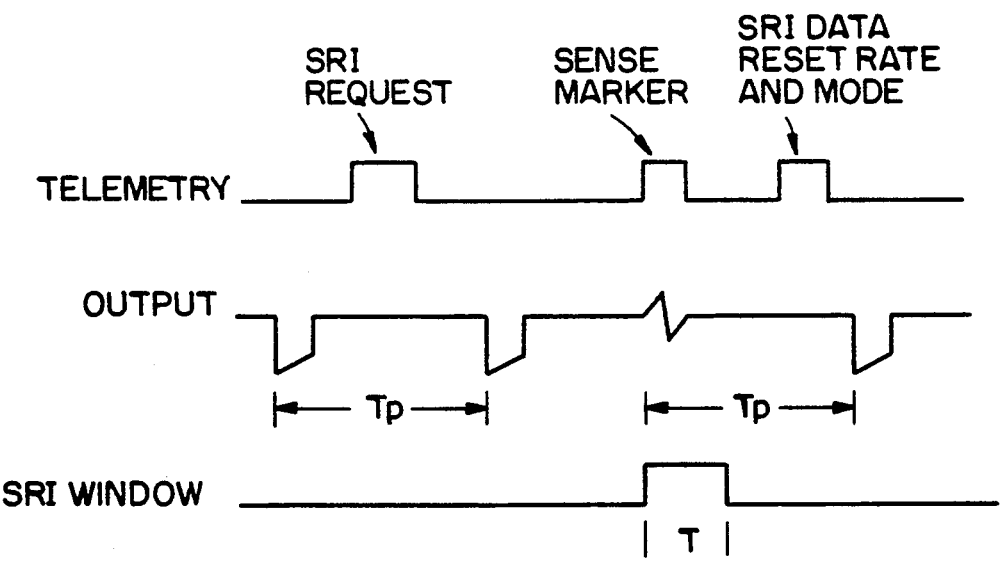
FIG. 12A is a timing diagram used in the automatic initialization routine of FIG. 12.

As indicated at 2,404, the software automatically requests the Sense Ratio Factor (SRF) feature, whereby the software calculates, on a cycle-by-cycle basis or once upon request, a ratio of signal level over the programmed threshold following the sense-amplifier detection. FIG. 12A is a timing diagram illustrating the SRF request and the SRF window "T", with respect to the pacemaker output and the programmed interval "$T_p$".

The SRF is calculated as follows:

$$SRF = \frac{(\text{Peak Sense})}{(\text{Sense Threshold}) \times (\text{Recommended Safety Margin})}$$

where the $$\text{Recommended Safety Margin} = \frac{[(\% \text{ Safety Margin} + 100\%)]}{100}$$

The software then automatically, temporarily switches the operating mode of the pacemaker 100 to VVI mode and sets the pacing rate to the lowest allowable rate, such as 30 pulse per minute (ppm). In this setting the pacemaker 100 is in a demand mode and the low pacing rate permits capture of a sensed event from an intrinsic depolarization.

Next, the software determines at 2,408, whether an event has been sensed during the 30 ppm escape interval. If it has not, then the pacing rate, the pacing mode and the sensitivity threshold are reset, at 2,412, to their original or programmed settings, prior to the initialization process, to ensure the safety of the patient. As shown in FIG. 12 at 2,410, the following message is displayed on the monitor 2,223, "Unable to Complete", indicating that the programmer 2,200 is unable to recommend a sensitivity threshold, and the physician has the option to either rerun the initialization routine at a later time, or to set the sensitivity threshold according to previous conventional practices.

Figure 12B:
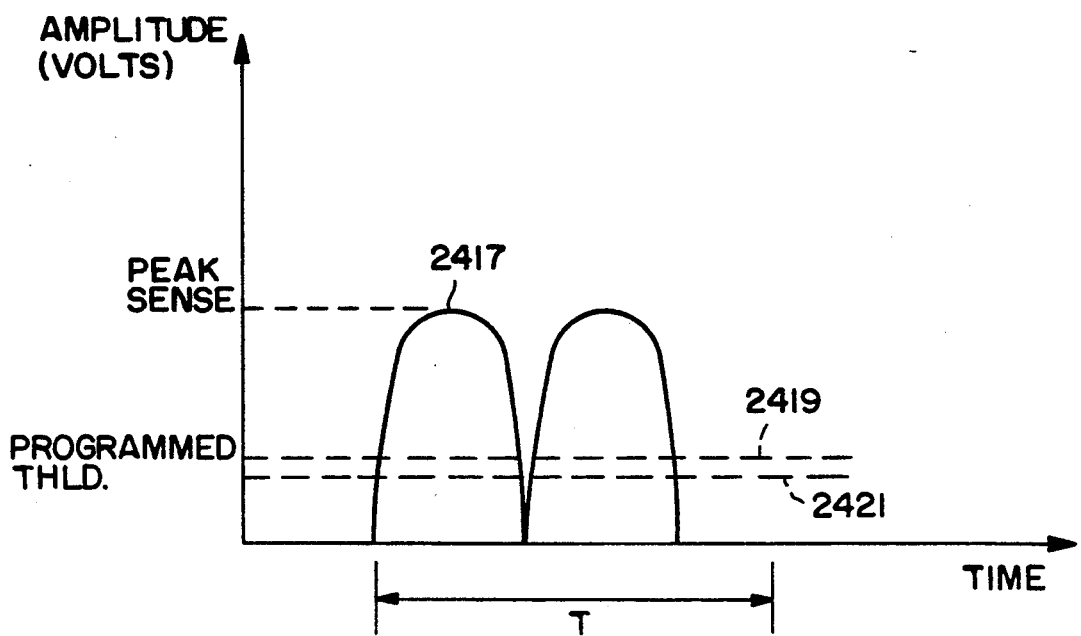
FIG. 12B is a graph showing the amplitude of the sensed events within a predetermined SRF window T, used in the automatic initialization routine of FIG. 12.

If at 2,408 an event is sensed, the software resets, at 2,414, the pacing rate, the pacing mode and the sensitivity threshold to their original or programmed settings. Then, as indicated by block 2,416, the peak sense and sensitivity threshold are uplinked from the pacemaker 100 to the programmer 2,200. FIG. 12B is a graph showing the amplitude of the sensed event within the SRF window T. Typically, T is set to about 110 msec. The peak sense is shown in FIG. 12B as 2,417. The value of the peak sense is digitized and automatically uplinked to the programmer 2,200. The measured sensitivity threshold 2,421 is uplinked to the programmer 2,200. This value is the actual measured value of the programmed threshold. Due to component variation, the programmed threshold may vary from its nominal value by ±20%. As further shown in FIG. 12B, the measured sensitivity threshold 2,421 is a value below which events are not sensed. A typical value for the programmed threshold is 2.5 millivolts (mV).

Next, the programmer 2,200 automatically retrieves the value of the safety margin, typically 200%. The safety margin is generally predesignated and preprogrammed to the desired value by each physician. However, the safety margin can be optionally modified by the physician at the onset of the initialization procedure.

The software then automatically calculates the recommended sensitivity threshold value, at 2,420, using the following equation:

Recommended Sensitivity
Threshold = $SRF \times$ Programmed Threshold.

The following example helps to better illustrate the initialization routine 2,400. If at block 2,416, the uplinked values of the measured peak sense and measured sensitivity threshold are 12 mV and 3 respectively; and the preprogrammed safety margin is 200 percent, then the SRF factor is:

$$(12 \text{ mv})/\left[(2.75 \text{ mV}) \times \frac{(200\% + 100\%)}{100}\right] = 1.45.$$

With a programmed sensitivity threshold of 2.5 mV, the recommended value for the sensitivity threshold becomes: (1.45)×(2.5 mV)=3.63 millivolts. Typically, the calculated sensitivity threshold value would be rounded down to the next most sensitive threshold setting, which, in the above example, is 3.5 mV.

After calculating the recommended value of the sensitivity threshold, the software determines at 2,422, whether the calculated SRF factor is greater or equal to six. If it is not, as it is illustrated in the above example, then the initialization routine is terminated, and the software returns to block 2,304.

If on the other hand, the SRF factor is greater than or equal to 6, then, as indicated at 2,424, the software temporarily calculates and sets the sensitivity threshold for a SRF factor of 4. The factor of 6 is selected to reflect the dynamic range of the sense amplifier used in the preferred embodiment. However, other values can be assigned to the SRF factor, depending on the type of the sense amplifier used. A temporarily programmed sensitivity threshold is then calculated:

$$\text{Temporary Sensitivity threshold} = \frac{\text{Peak Sense}}{4 \times \text{Safety Margin}},$$

rounded up to the next highest threshold setting, and temporarily programmed at 2,424 as noted above.

Thereafter, the software returns to block 2,406 and repeats the subroutine 2,406 through 2,422, with the SRF factor near 4.

Figure 13:
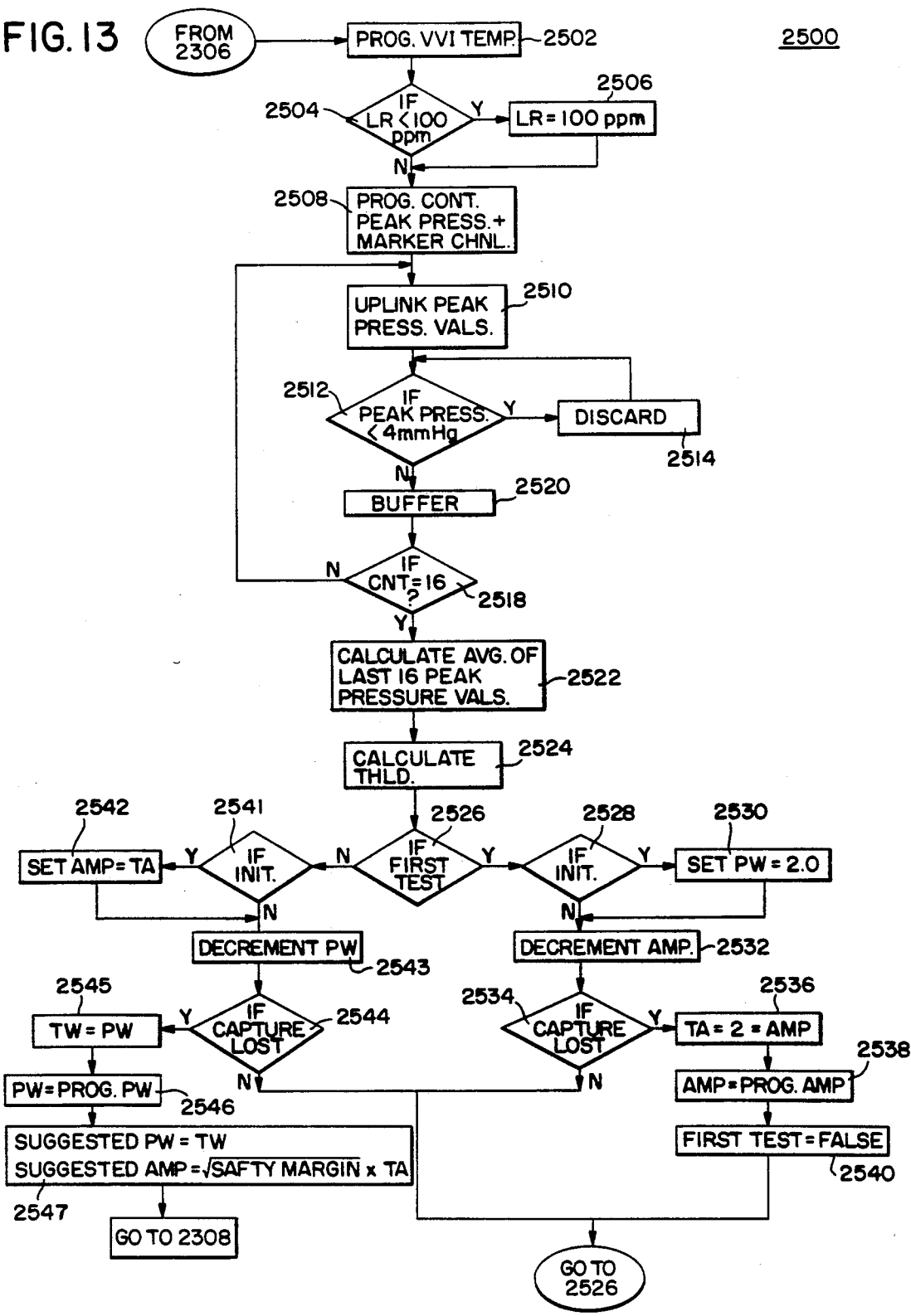
FIG. 13 is a simplified flow chart illustrating an automatic initialization routine for selecting the optimal pulse width and amplitude parameters according to the present invention.

Turning now to FIG. 13 of the drawings, there is illustrated, in a simplified flow chart format, the automatic initialization routine 2,500 for selecting the optimal pulse width and amplitude parameters. The object of this initialization routine 2,500 is to recommend the settings for the pulse amplitude and width which cause minimal current drain on the battery source, and thus leading to an increased longevity of the battery, while simultaneously retaining the desired safety margin.

The software starts the initialization routine 2,500 at 2,502, by automatically, temporarily switching the operating mode of the pacemaker 100 to VVI mode. Next, the software determines at 2,504 whether the programmed lower rate is lower than 100 ppm. If it is, then, as indicated at block 2,506, the lower rate is temporarily set to 100 ppm, in order to shorten the initialization period, and to ensure a sequence of paced pulses.

If on the other hand, the lower rate is found to be greater than 100 ppm, then, the software leaves the software unchanged. The software then instructs the pacemaker 100 at 2,508, to continuously uplink peak pressure telemetry values, as valid values, and to turn on the marker channel. The peak pressure values are then uplinked to the programmer 2,200, at 2,510, and the software determines at 2,512, whether the peak pressure is less than 4 millimeters of Mercury (mm Hg).

If it is, then the software discards these values, as indicated at 2,514. If at block 2,512 the peak pressure is found to be greater than 4 mm Hg, then the peak value is saved at 2,520. The software then determines at 2,518 whether the total count of the valid pressure peaks is equal to 16. If it is not, then the software returns to block 2,510, and repeats the subroutine until the count is equal to 16.

The software then calculates the average peak pressure over the last sixteen peak pressure value at 2,522, and the pressure threshold is calculated at 2,524, as follows:

Recommended Threshold = Average Peak Pressure
Value × Programmed Threshold where the value of the Programmed Threshold may vary from 25-75% and is typically 37½%.

Figure 13A:
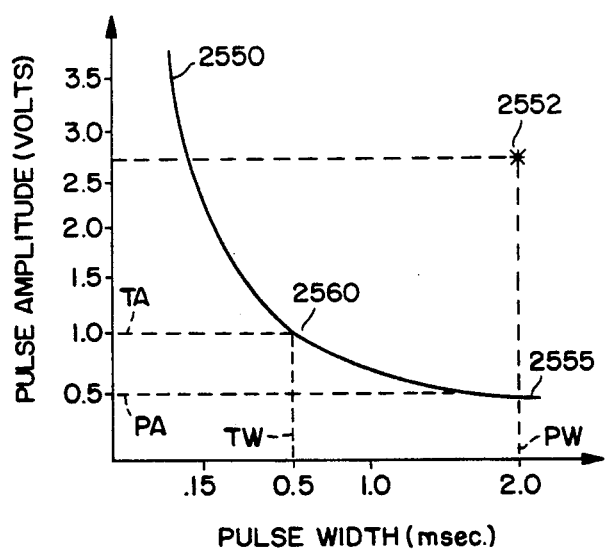
FIG. 13A is a strength duration curve used in the automatic initialization routine of FIG. 13.

The software then determines at 2,526, whether this is the first test, that is whether the rheobase will be determined. The remainder of the initialization routine 2,500 will now be described also in relation to FIG. 13A, which illustrates a typical strength duration curve 2,550. The vertical axis in FIG. 13A represents the pulse amplitude in Volts, and the horizontal axis represents pulse width in milliseconds.

The software then determines at 2,528 whether this is the initial pulse of this test. If it is, then the software sets the pulse width to 2.0 msec at 2,530. Let us consider for illustration purposes that the point 2,552 is the initial setting. Point 2,552 is located above the strength duration curve 2,550, and the event is captured. It is the purpose of the present initialization routine to find the rheobase 2,555, which is defined as the last capture point on the strength duration curve, at a pulse width of 2 msec.

In order to find the rheobase 2,555, the software decrements the amplitude, as indicated at 2,532, until capture is lost. This is accomplished by the software which inquires at 2,534 whether capture is lost, and if it has not, then the software repeats the subroutine until capture is lost, and the pulse amplitude (PA) of the rheobase is determined. In the present example, PA is found to be equal to 0.5 volts.

When at 2,534, it is determined that capture is lost, then the software sets forth to define the chronaxie 2,560. The chronaxie is defined as the last capture point on the strength duration curve 2,550 having a pulse amplitude (TA) equal to twice the amplitude (PA) of the rheobase.

For this purpose, the software calculates TA=2-×PA, as indicated at block 2,536; then resets amplitude to programmed amplitude to the pacemaker 100 at 2,538; thereafter sets the following flag: "First Test-=False" at 2,540; and then returns to block 2,526. Due to this flag, the software then determines at 2,526 that this is the second test and that it is the chronaxie that should be determined. The software then determines at 2,541 if this is the initial pulse of the second test. If it is, then the software sets the pulse amplitude to TA (i.e. 1.0 volt in the above example), at 2,542, and then decrements the pulse width until the chronaxie is located on the strength duration curve 2,560.

This is accomplished by inquiring at 2,544, whether capture is lost. If it is not, then the software returns to block 2,526, and the subroutine is repeated until capture is lost. At which point the software sets the pulse width to TW, that is the pulse width of the chronaxie. In the above example TW=0.5 msec. The programmed value of pulse width is then reset in the pacemaker 100, at 2,546.

The programmer then recommends at 2,547, the following values for the pulse width and amplitude:

Recommended Pulse Width=Pulse Width of the Chronaxie (PW);

and

Recommended Pulse Amplitude=$k \times$ the Pulse Amplitude of the chronaxie (TA), where the "k" coefficient is equal to the square root of the safety margin.

Figure 13B:
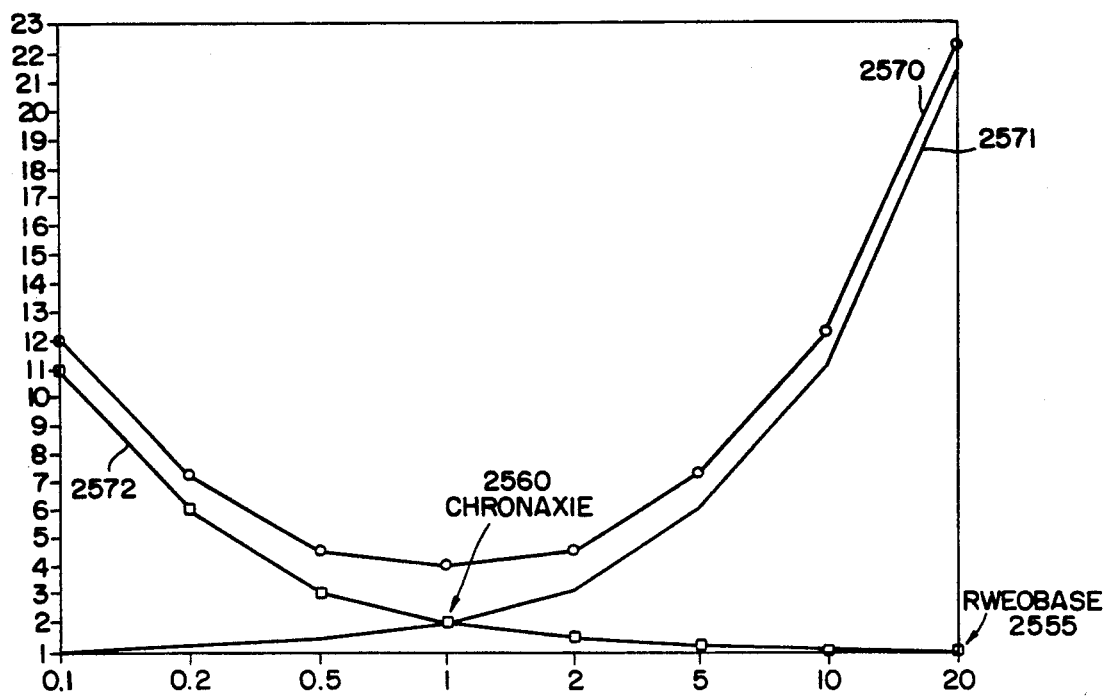
FIG. 13B illustrates three optimized output parameters curves used in the automatic initialization routine of FIG. 13.

The "k" coefficient has been found to be the optimal coefficient, by using the optimized output parameters curves 2,570, 2,571 and 2,572 illustrated in FIG. 13B. The horizontal axis represents the pulse width value normalized to the pulse width at chronaxie. The vertical axis represents the output intensity 2,572 normalized to the stimulation threshold at rheobase. The charge delivered 2,571 and energy delivered for stimulation 2,570 are also shown. As indicated in FIG. 13B, the minimum energy required for stimulation is at the pulse width at chronaxie.

Figure 14:
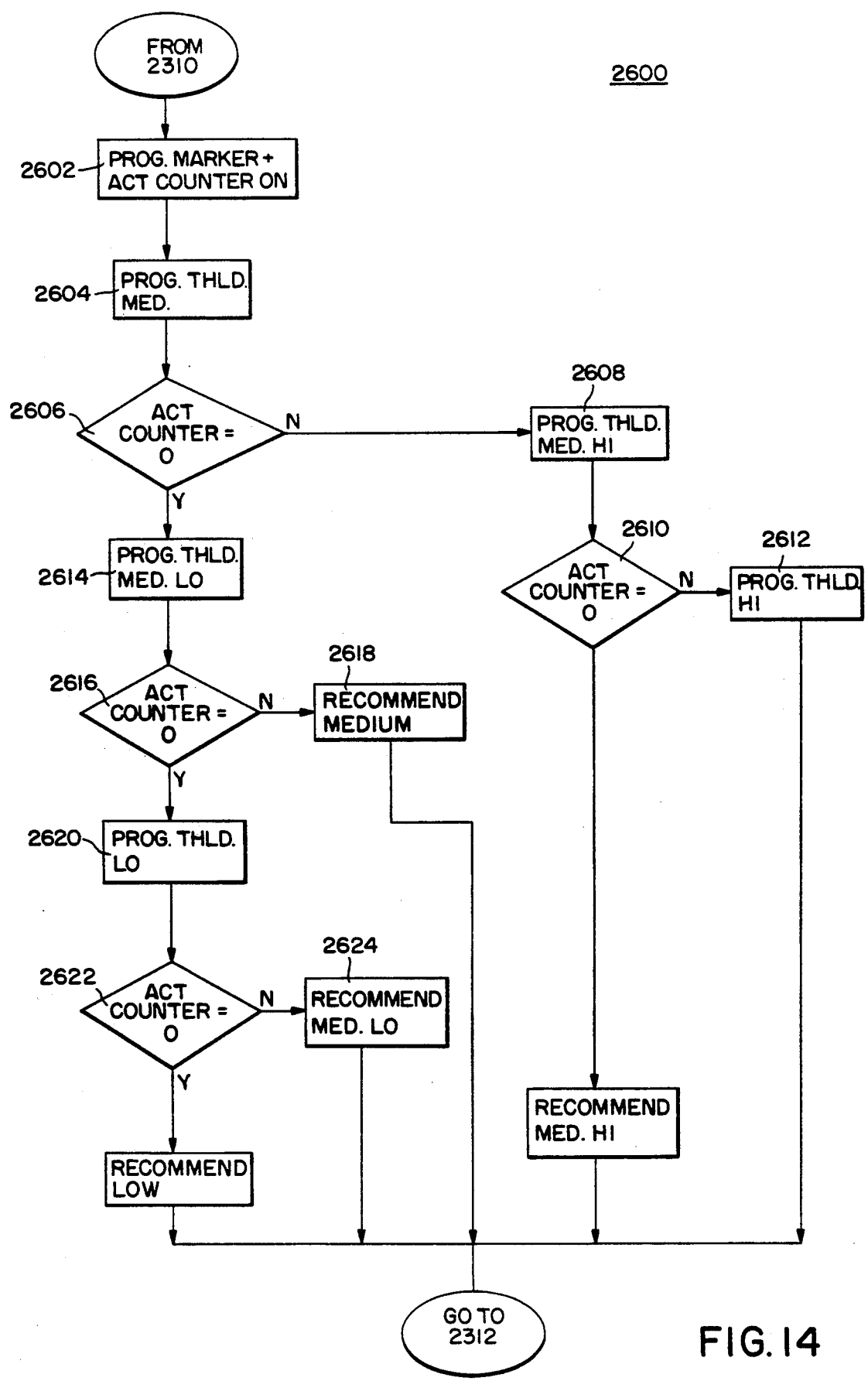
FIG. 14 is a simplified flow chart illustrating an automatic initialization routine for selecting the optimal activity threshold value in accordance with the present invention.

Turning now to FIG. 14, there is illustrated, in a simplified flow chart format, the automatic initialization routine 2,600 for selecting the optimal activity threshold value. The object of this initialization routine 2,600 is to recommend the maximum activity threshold setting without getting an activity count, since the patient is in a resting position during the initialization routine 2,600.

The pacemaker 100 includes 5 settings: LOW, MEDIUM LOW, MEDIUM, MEDIUM HIGH AND HIGH, which correspond to the possible level settings that are make available by the pacemaker 100. The initialization routine 2,600 automatically recommends the appropriate setting to the physician. The software starts the initialization routine 2,600 at 2,602, by automatically enabling the marker channel as described above, and by setting the activity count telemetry ON. The pacemaker 100 is then set to the MEDIUM activity threshold, as indicated at 2,604, and the activity counter starts counting the sensed activity events with values uplink via telemetry every 2 seconds.

If at 2,606 the software determines that the activity count is different than zero, then the activity threshold is automatically programmed to the MEDIUM HIGH setting at 2,608. If at 2,610 the counter indicates that the activity count is equal to zero, then the software recommends the MEDIUM HIGH setting and returns to block 2,312.

If on the other hand the activity count at 2,610 is not equal to zero, then, as indicated by block 2,612, the activity threshold is automatically programmed to the HIGH setting, and the software recommends the HIGH setting and returns to block 2,312.

If at block 2,606 it is determined that the activity count is equal to zero, then the activity threshold is changed to the MEDIUM LOW setting at 2,614, and the software inquires once again, at 2,616, whether the activity count is equal to zero. If it is not, then as indicated at 2,618, the software recommends the MEDIUM setting as the optimal activity threshold setting, and returns to block 2,312.

If at 2,616, the activity count is equal to zero, then the activity threshold is programmed to the LOW setting at 2,620, and the software inquires once again, at 2,622, whether the activity count is equal to zero. If it is, then the software recommends the LOW setting as the optimal activity threshold setting, and returns to block 2,312.

If the software determines at 2,622 that the activity count is not equal to zero, then the software recommends the MEDIUM LOW setting as the optimal activity threshold setting, and returns to block 2,312.

Figure 15:
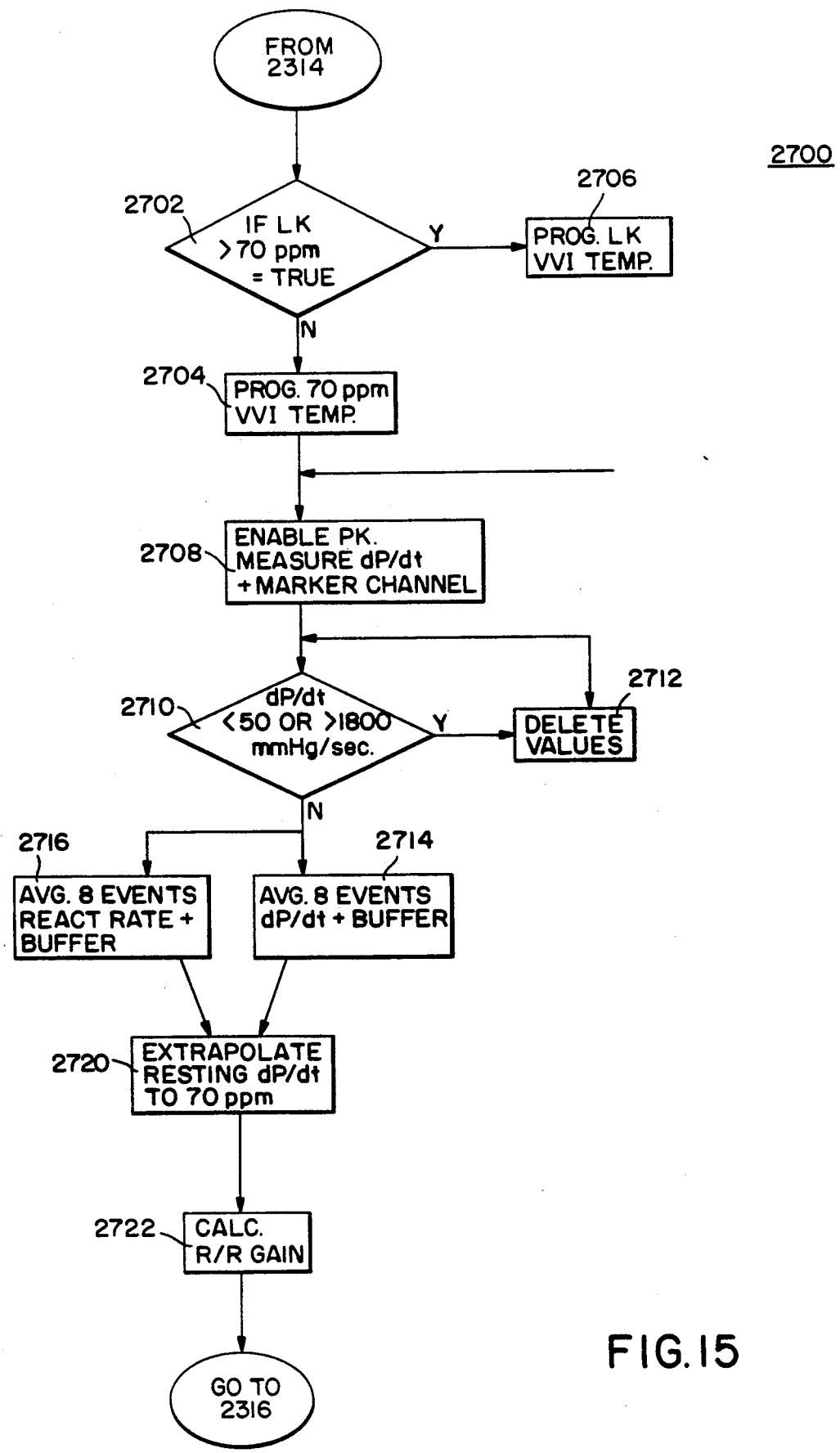
FIG. 15 is a simplified flow chart illustrating an automatic initialization routine for selecting the optimal pressure rate response gain setting, in accordance with the present invention.

Turning now to FIG. 15, there is illustrated, in a simplified flow chart format, the automatic initilization routine 2,700 for selecting the optimal pressure rate response gain setting. The object of this initialization routine 2,700 is to recommend a dP/dt rate response gain curve based upon the lower rate/upper rate and an extrapolated resting dP/dt value.

The software starts the initialization routine 2,700 at 2,702 by inquiring whether the lower rate is greater than 70 ppm. If it is not, then the software automatically and temporarily sets the pacing rate to 70 ppm, and changes the pacing mode to VVI mode, at 2,704. If on the hand the lower rate is greater than 70 ppm, then the software changes the pacing mode to VVI mode, at 2,706, thus leaving the lower rate at its programmed value.

The software then enables the dP/dt peak measurement feature as well as the marker channel, and the pacemaker 100 starts to automatically uplink via telemetry, at 2,708, the peak dP/dt values of the pressure pulses at the occurrence of each paced or sensed event.

The software then inquires at 2,710 whether the uplinked dP/dt value ranges between 50 mm Hg and 1800 mm Hg. If it does not, then, as indicated at 2,712, the measured dP/dt value is rejected as being an artifact, and the software once again makes the same inquiry at 2,710. If the uplinked dP/dt value ranges between 50 mm Hg and 1800 mm Hg, then this value is saved and the software goes through the same subroutine, until the 8 events are accounted for.

Thereupon, the software simultaneously calculates the average peak dP/dt over the last 8 events, at 2,714, and the average rate over these same last events, at 2,716. As defined herein, the resting dP/dt is the arithmetic mean of the peak positive dP/dt measured during a predetermined interval of 8 paced/sensed events with the patient at rest. The resting rate is the arithmetic mean of the paced or intrinsic rate over a predetermined interval of 8 paced/sensed events with the patient at rest.

The software then automatically extrapolates the resting dP/dt to 70 ppm, as follows:

Resting $dP/dt$=[70 ppm$\times$Average Peak $dP/dt$]/Average Resting Rate.

Once the extrapolated resting dP/dt value is found, the software sets the 15 rate response gain as follows:

$$\text{Rate Response Gain} = \frac{\text{Upper Rate} - \text{Resting Rate}}{\text{Resting } dP/dt}$$

The software then recommends one of the ten rate response curves shown in FIG. 6A, and returns to 2,316.

It can be seen that the Target Rate (TR) for each sensor is thus a function of the respective sensor's output, which functional correlation is defined in more detail below. These Target Rates are utilized by the pacemaker 100 in deriving the rate-responsive pacing rate for the patient's heart.

While particular embodiments of the present invention have been disclosed, it is to be understood that various different modifications are possible and are contemplated within the scope of the specification, drawings, abstract and appended claims.

What is claimed is:

1. A pacemaker system for automatically optimizing and initializing pacing parameters in a pacemaker, comprising:
   a. optimizing means for automatically initializing a sensitivity threshold parameter;
   b. means, responsive to said optimizing means, for displaying said initialized sensitivity threshold parameter; and
   c. said optimizing means including:
      i) means for periodically calculating a sense ratio factor (SRF) according to the following equation:

$$SRF = \frac{(\text{Peak Sense})}{(\text{Sense Threshold}) \times (\text{Recommended Safety Margin})}$$

where the Recommended Safety Margin is calculated as follows:

$$\text{Recommended Safety Margin} = \frac{(\% \text{ Safety Margin} + P \%)}{100}$$

and where the Safety Margin and P are programmable values; and
      ii) means for determining said initialized sensitivity threshold according to the following equation:

$$\frac{\text{Recommended}}{\text{Sensitivity Threshold}} = SRF \times \text{Programmed Threshold}.$$

2. A pacemaker system for automatically optimizing and initializing pacing parameters in a pacemaker, comprising pulse optimizing means, the improvement being characterized in that said pulse width optimizing means includes:
   i) means for determining a rheobase point along a strength duration curve;
   ii) means for determining a chronaxie point based on said rheobase point; and
   iii) means for determining a pulse width parameter according to the following equation:

Recommended Pulse Width = Pulse Width of the Chronaxie.

3. The pacemaker system as defined in claim 2, further including pulse amplitude optimizing means for automatically initializing a pacing pulse amplitude parameter; and
   wherein said pulse amplitude optimizing means includes means for determining said initialized pulse amplitude parameter according to the following equation:

Pulse Amplitude = $k \times$ Pulse Amplitude of Chronaxie, where "k" is a programmable coefficient.

4. The pacemaker system as defined in claim 3, wherein said coefficient "k" is equal to the square root of the safety margin.

5. A pacemaker system for automatically optimizing and initializing pacing parameters in a pacemaker, characterized in that it includes:
   a. optimizing means for automatically initializing an activity threshold parameter;
   b. means, responsive to said optimizing means, for displaying said initialized activity threshold parameter;
   c. said optimizing means including:
      i) means for setting the activity threshold to an initial setting;
      ii) means for periodically counting sensed activity events at rest; and
      iii) means for automatically selecting one of a plurality of higher settings for said activity threshold, if said counting means indicates a positive activity count.

6. The pacemaker system as defined in claim 5, wherein said optimizing means further includes means for automatically selecting one of a plurality of lower settings for said activity threshold, if said counting means indicates a zero activity count.

7. A pacemaker system for automatically optimizing and initializing pacing parameters in a pacemaker, comprising:
   a. optimizing means for automatically initializing a pressure rate response gain threshold parameter;
   b. means, responsive to said optimizing means, for displaying said initialized pressure rate response gain threshold parameter; and
   c. said optimizing means including:
      i) means for counting and measuring valid peak pressure values (dP/dt);
      ii) means for averaging said peak pressure values over a predetermined interval of time;
      iii) means for calculating a resting pressure value according to the following equation:

$$\text{Resting } dP/dt = \frac{[M \times \text{Average Peak } dP/dt]}{\text{Average Resting Rate}},$$

where M is a programmable value in pulses per minute; and
      iv) means for extrapolating said resting pressure value to calculate the rate response gain setting, as follows:

$$\text{Rate Response Gain} = \frac{\text{Upper Rate} - \text{Resting Rate}}{\text{Resting } dP/dt}.$$

8. A pacemaker system for automatically and simultaneously optimizing and initializing pacing a plurality of parameters in a pacemaker, comprising:
   a. first optimizing means for automatically initializing a sensitivity threshold parameter;
   b. second optimizing means for automatically initializing the pacing pulse width parameter;
   c. third means for automatically initializing a pacing pulse amplitude parameter;
   d. fourth optimizing means for automatically initializing an activity threshold parameter; and
   e. fifth optimizing means for automatically initializing a pressure rate response gain threshold parameter.

9. A cardiac pacemaker of the type comprising a pulse generator for generating stimulus pulses characterized in that it includes:
   a. means for selecting a set of predetermined achievement criteria;
   b. means for selecting a first pacing switch rate threshold;
   c. means for determining whether said achievement criteria have been met; and d. means for modifying the decay time constant of the decay curve from a first value to a second value, if said achievement criteria have been met, as the pacing rate drops below said first pacing switch rate threshold, such that said second value is different from said first value.

10. The pacemaker as defined in claim 9, further including:
 a. means for selecting a second pacing switch rate threshold lower than said first pacing switch rate threshold; and
 b. means for modifying the decay time constant of the decay curve from the second value to a third value, if said achievement criteria have been met, as the pacing rate drops below said second pacing switch rate threshold, such that said second value is different from said third value.

11. The pacemaker as defined in claim 10, wherein said second value of the time constant for the decay curve is lower than said first value, in order to allow a slower decay of the pacing rate.

12. The pacemaker as defined in claim 10, wherein said first pacing switch rate threshold is calculated as follows:

$$\text{First Pacing Switch Rate} = \text{Lower Rate} + u(\text{Upper Rate} - \text{Lower Rate}).$$

13. The pacemaker as defined in claim 12, wherein said second pacing switch rate threshold is calculated as follows:

$$\text{Second Pacing Switch Rate} = \text{Lower Rate} + 10\% \text{ Lower Rate}.$$

14. The method as defined in any one of claims 9 through 13 further including means for calculating a target rate according to the following equation:

$$TR = \frac{(\text{Activity Count} + D)}{C} * (32768 * 60/328),$$

where C and D are selectively programmable values.

15. The pacemaker as defined in claim 9, wherein said achievement criteria includes an achievement rate and an achievement time interval; and wherein said achievement rate is selected between an upper pacing rate and said first pacing switch rate.

16. The pacemaker as defined in any one of claims 9, 10, 11 or 15, wherein said achievement rate is calculated as follows:

$$\text{Achievement Rate} = \text{Lower Rate} + a(\text{Upper Rate} - \text{Lower Rate}),$$

where "a" is a percentile value which ranges between 50% and 100%, and the Lower Rate and the Upper Rate are the lower and upper pacing rates respectively.

* * * * *

UNITED STATES PATENT AND TRADEMARK OFFICE
CERTIFICATE OF CORRECTION

PATENT NO. : 5,158,078
DATED : 27 October 1992
INVENTOR(S) : Bennett, Tommy D., Nicols, Lucy M, Thompson, David, Roline, Glenn.

It is certified that error appears in the above-indentified patent and that said Letters Patent is hereby corrected as shown below:

```
On the title page, item [75] should read
--Inventors:  Tommy D. Bennett, Shoreview, Lucy M. Nichols, Maple
Grove, Glenn M. Roline, Anoka, David L. Thompson, Fridley, all of
Minnesota.
```

Signed and Sealed this

Twenty-third Day of November, 1993

Attest:

BRUCE LEHMAN

*Attesting Officer*   *Commissioner of Patents and Trademarks*